(12) United States Patent
Tan et al.

(10) Patent No.: US 10,457,780 B2
(45) Date of Patent: Oct. 29, 2019

(54) HYGROMORPHIC POLYMERS AND COPOLYMERS HAVING HUMIDITY-DRIVEN MOTILITY

(71) Applicant: Government of the United States, as represented by the Secretary of the Air Force, Wright-Patterson AFB, OH (US)

(72) Inventors: Loon-Seng Tan, Centerville, OH (US); David Huabin Wang, Beavercreek, OH (US); Richard A. Vaia, Beavercreek, OH (US); Philip R Buskohl, Beavercreek, OH (US); Ruel McKenzie, Akron, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 116 days.

(21) Appl. No.: 15/910,094

(22) Filed: Mar. 2, 2018

(65) Prior Publication Data
US 2018/0194898 A1 Jul. 12, 2018

Related U.S. Application Data

(62) Division of application No. 15/076,810, filed on Mar. 22, 2016, now Pat. No. 9,932,445.

(60) Provisional application No. 62/306,695, filed on Mar. 11, 2016.

(51) Int. Cl.
| | | |
|---|---|---|
| *C08G 73/14* | (2006.01) | |
| *C08G 73/10* | (2006.01) | |
| *C08G 69/32* | (2006.01) | |
| *C07C 317/44* | (2006.01) | |
| *C07C 315/04* | (2006.01) | |
| *C07C 315/00* | (2006.01) | |
| *C07C 317/18* | (2006.01) | |
| *C07C 317/40* | (2006.01) | |
| *C08G 69/42* | (2006.01) | |
| *C07C 229/56* | (2006.01) | |

(52) U.S. Cl.
CPC ........ *C08G 73/1085* (2013.01); *C07C 315/00* (2013.01); *C07C 315/04* (2013.01); *C07C 317/18* (2013.01); *C07C 317/40* (2013.01); *C07C 317/44* (2013.01); *C08G 69/32* (2013.01); *C08G 69/42* (2013.01); *C08G 73/1039* (2013.01); *C08G 73/1042* (2013.01); *C08G 73/1067* (2013.01); *C08G 73/1071* (2013.01); *C08G 73/14* (2013.01); *C07C 229/56* (2013.01)

(58) Field of Classification Search
CPC ...... C08L 79/08; C08G 73/1064; C08G 73/14
See application file for complete search history.

(56) References Cited

FOREIGN PATENT DOCUMENTS

JP  11-149099  *  6/1999

* cited by examiner

*Primary Examiner* — Gregory Listvoyb
(74) *Attorney, Agent, or Firm* — AFMCLO/JAZ; Chastity Whitaker

(57) ABSTRACT

New diamine monomers bearing sulfone terminated pendant groups, as well as methods for making the same, are provided. The diamine monomers are useful toward making polyamide, polyimide, and poly(amide-imide) polymers and copolymers, which possess hygromorphic properties and demonstrate humidity driven motility.

13 Claims, 16 Drawing Sheets

HYGROMORPHIC POLYMERS AND COPOLYMERS HAVING HUMIDITY-DRIVEN MOTILITY

CROSS-REFERENCE TO RELATED APPLICATIONS

The present application is a divisional application of U.S. application Ser. No. 15/076,810, which was filed Mar. 22, 2016, which claims priority to U.S. Provisional Patent Application Ser. No. 62/306,695 entitled "Polymers and Thermally Derived Copolymers with Hygromorphic Effect and Humidity-Driven Motility," filed on Mar. 11, 2016. The disclosure of each of these applications is incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The invention generally relates to hygromorphic polymers and copolymers. More particularly, the invention relates to polyimide, polyamide, and poly(amide-imide) polymers and copolymers containing ester-sulfone and/or amide-sulfone as pendant chains, which demonstrate hygromorphic- and humidity-driven motility properties, and methods of making the same.

BACKGROUND

An actuator is a mechanical device that is powered by a certain source of energy, such as electric current, pressure and chemical energy, and can transform that energy into motion. According to the energy source utilized for actuation, responsive polymeric materials generally can be divided into three classes: electro-active polymers; light- or heat-responsive elastomers; and pH- or solvent-responsive gels.

Technologically, an actuator with controlled and directed motions upon application of a stimulus is particularly attractive because such a device could mimic organisms, and has numerous applications ranging from sensors, switches, and artificial muscles to nano/micro electromechanical systems. In a specific area, the actuation and power-generation systems that can harvest ambient energy from water gradients have recently attracted a great deal of attention, especially in the development of "dry" or liquid-free polymer actuators based on conducting polymers (CP) such as polypyrroles (PPy), polythiophenes, and polyanilines (PANI) as well as their composite systems. Thus, high hydrophilicity of the doped state, as well as the stress-strain generated from movement of water molecules directed by humidity variation, are being exploited.

For example, the doped PPy film containing perchlorate counter-ions would undergo rapid bending upon asymmetrical water-vapor sorption, and would crawl on a wet filter paper; culminating in the designs of a soft motor capable of directly transducing chemical potential of water sorption into a continuous circular motion, and origami (folded PPy film) actuators. Furthermore, the doped PPy film would contract in air under an applied voltage, thus generating Joule heating to desorb water molecules and providing an electromechanical control of the device.

In an alternative design in which semi-solid polyelectrolye had been used, a polymer composite film based on polypyrrole-polyolborate (PPy-POB) was shown to spontaneously and reversibly capture and release the ambient water vapor to induce film expansion and contraction, resulting in rapid and continuous locomotion on a wet surface. The PPy-POB machine was strong and powerful enough to lift objects 380 times heavier than itself, and transport cargo 10 times heavier than itself.

Another version of dry CP-actuators based on a polythiophene, viz. commercially available poly(3,4-ethylenedioxythiophene)/polystyrenesulfonate (PEDOT:PSS), has been fabricated, wherein a nontraditional bilayer design with a collective capillarity feature to create the effect of asymmetric water diffusion. This PEDOT:PSS composite material is comprised of doped polyaniline (PANI) nanotubes chemically synthesized in-situ and embedded in a polycarbonate membrane, with one end of the nanotubes attached to a subsequently surface-deposited PANI layer. The so-called "nanotubes embedded membrane" (NEM) showed water diffusion behavior quite similar to those observed for biological ion channels and pumps, and displayed excellent moisture-propelled oscillatory motion, and artificial-muscle capability.

From the standpoint of dielectric materials, innovative approaches to humidity-driven actuation take advantage of the stress-strain generated from the orientational change in liquid-crystalline polymers (LCP) and networks (LCN) containing moieties (e.g., OH and COOH) that are sensitive to polar solvent vapors. As lyotropic or thermotropic LCP, cellulose derivatives, such as partially hydroxypropylated cellulose (HPC) and partially modified cellulose stearoyl ester (CSE) may have networks with solid state properties similar to LCE and LCN. Their solution-cast films are hygroscopic and have been shown to be promising materials in the development of humidity-powered, soft motors.

Building on a hygroscopic and mechanically robust liquid crystal network (LCN) polymer containing COOH groups that are capable of reversible hydrogen-bonding and become hydrophilic after alkaline treatment, another family of humidity actuators has been created. These new humidity-driven actuators may be in monolithic form or in bilayer configuration with a uniaxially oriented polyamide-6 substrate, and having large responses to humidity change as manifested in bending, folding, and curling motions. Bilayer actuators based on alternating layer-by-layer deposition of poly(cation)/poly(anion) films on hydrophobic polymer substrates and engineered to power devices capable of unidirectional and humidity-controllable locomotion on a ratchet track have also been described.

While the above-mentioned examples for humidity-driven actuators have illustrated several innovative bilayer designs and clever utilization of responsive polymeric and nanocomposite systems, it appears that no simple, wholly covalent polymer in monolithic form with hygromorphic and motile properties has been reported. Accordingly there is a need for new polymers and copolymers with hygromorphic and motile properties, as well as new methods for making them.

SUMMARY OF THE INVENTION

New diamine monomers bearing sulfone-terminated pendant groups, as well as methods for making same, are provided. The diamine monomers are useful toward making polyamide, polyimide, and poly(amide-imide) polymers and copolymers, which possess hygromorphic properties and demonstrate humidity driven motility.

Thus, in accordance with an embodiment of the present invention, an aryl diamine monomer is provided that comprises a sulfone moiety and has a general chemical formula:

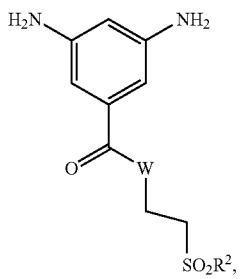

wherein W is selected from the group consisting of O, NH, and $NR^1$, wherein $R^1$ and $R^2$ are independently selected from the group consisting of substituted or unsubstituted C1-C7 alkyl groups, and substituted or unsubstituted phenyl groups, with the proviso that $R^2$ is not methyl when W is O.

In accordance with another embodiment of the present invention, a method of synthesizing the aryl diamine monomer is provided, the method comprises reducing a bis-nitroaryl moiety comprising a sulfone moiety and having a general formula:

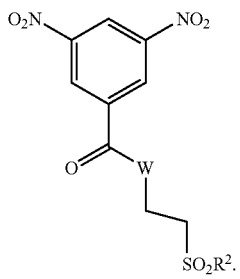

The bis-nitro aryl moiety may be obtained directly or indirectly by reacting 3,5-dinitrobenzoic acid or 3,5-dinitrobenzoic acid halide with an ethyl sulfonyl moiety having a general formula:

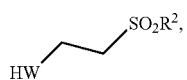

where W and $R^2$ are defined above.

In accordance with yet another embodiment of the present invention, a polymer is provided that comprises a diamine portion derived from the aryl diamine monomer comprising the sulfone moiety, wherein the polymer is selected from the group consisting of a polyamide, a polyimide, and a poly(amide-imide).

In accordance with yet another embodiment of the present invention, a copolymer composition is provided that includes complementary monomer portions of a first monomer portion comprising a sulfone terminated pendant group and having a general formula:

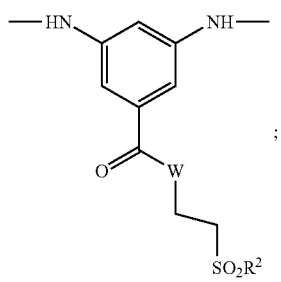

a second monomer portion comprising a carboxylic acid or carboxamide terminated pendant group and having a general formula:

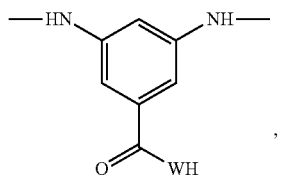

wherein W is selected from the group consisting of O, NH, and $NR^1$, wherein $R^1$ and $R^2$ are independently selected from the group consisting of substituted or unsubstituted C1-C7 alkyl groups, and substituted or unsubstituted phenyl groups; and wherein the copolymer is selected from the group consisting of a polyamide copolymer, a polyimide copolymer, and a poly(amide-imide) copolymer.

Advantageously, many of the materials utilized in the syntheses are readily available and cost-effective, allowing for scalability. Moreover, the polymers and copolymers incorporating the hydrophilic the sulfone moiety possess hygromorphic properties and demonstrate humidity driven motility. Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIG. 14a is a schematic of the steady state humidity gradient cell where dC/dz is the humidity gradient in the cell and arrows indicate direction of flux; and FIG. 14b shows an effect of side chain and backbone on film curvature, where a trace is added for clarity.

It should be understood that the appended drawings are not necessarily to scale, presenting a somewhat simplified representation of various features illustrative of the basic principles of the invention. The specific design features of the sequence of operations as disclosed herein, including, for example, specific reagents, solvent, catalysts, and/or reaction conditions, will be determined in part by the particular intended application and use environment.

DETAILED DESCRIPTION OF EMBODIMENTS OF THE INVENTION

As part of ongoing research on adaptive polyimide-based systems that have been shown to be mechanically responsive to light, heat and thermal-electrical stimuli, herein new sulfone-containing polyimide, polyamide, and poly(amide-imide) polymers and related thermally-derived copolymers. Further disclosed are the mechanical responsivities relative to structurally similar polymers containing $CO_2H$-pendants in a humidity gradient, information which may be useful toward developing adaptive structures that are functional in both dry and wet environments.

Thus in accordance with an embodiment of the present invention, a new diamine monomer bearing sulfone-terminated pendant groups, as well as methods for making same, are provided. The diamine monomer is useful toward making polyamide, polyimide, and poly(amide-imide) polymers and copolymers, which possess hygromorphic properties and demonstrate humidity driven motility. More specifically, an aryl diamine monomer is provided that comprises a sulfone moiety and has a general chemical formula:

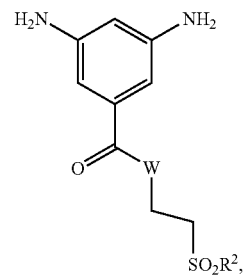

wherein W is selected from the group consisting of O, NH, and $NR^1$, wherein $R^1$ and $R^2$ are independently selected from the group consisting of substituted or unsubstituted C1-C7 alkyl groups, and substituted or unsubstituted phenyl groups, with the proviso that $R^2$ is not a methyl when W is O.

Figure 1:
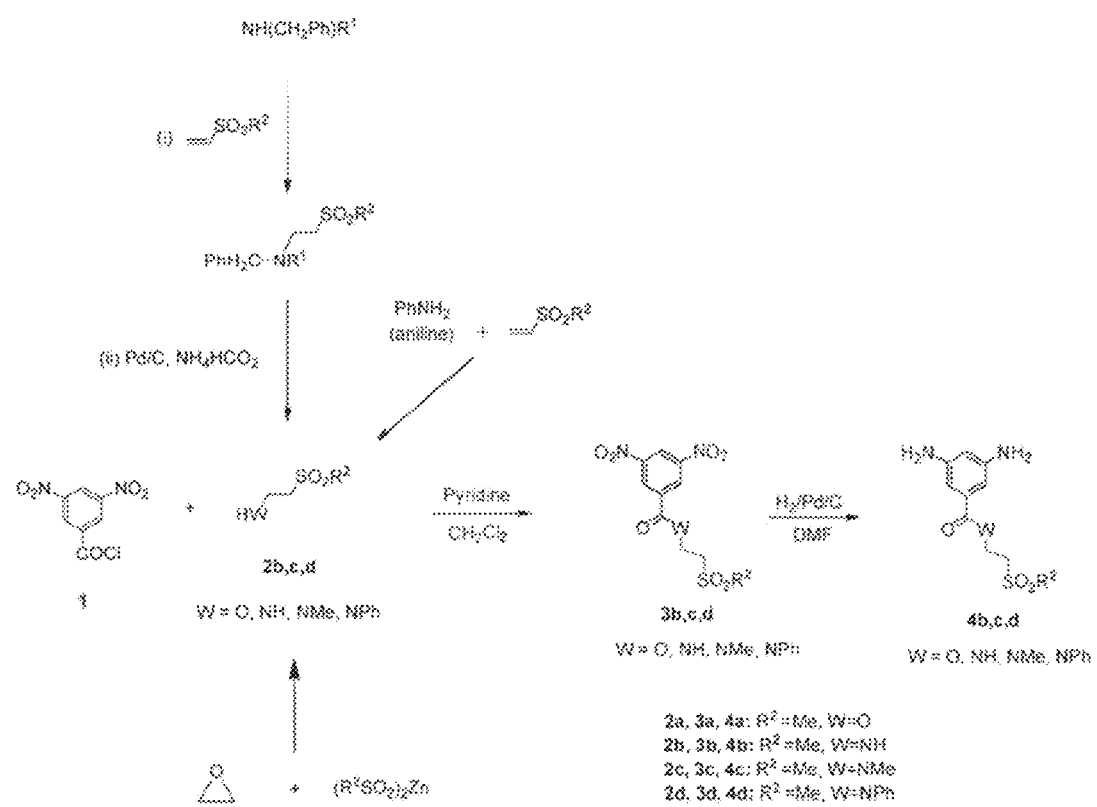
FIG. 1 is a schematic showing a synthetic route for preparing the aryl diamine monomer comprising a sulfone moiety that is incorporated into the hygromorphic polymers and copolymers, in accordance with an embodiment of the present invention.

In FIG. 1, exemplary synthetic routes to preparing the aryl diamine monomer are provided. In an embodiment, esterification of 3,5-dinitrobenzoyl chloride (1) with a suitable sulfone-substituted ethyl alcohol derivative (FIG. 1, W=O, compound 2a) provides the corresponding 3,5-dinitrobenzoate ester (3a), which is followed by reduction of the nitro groups to provide the corresponding 3,5-diaminobenzoate ester (4a). For example, esterification of 3,5-dinitrobenzoyl chloride (1) with 2-(methylsulfonyl)ethanol (FIG. 1, compound 2a, where W=O, $R^2$=Me) affords 2-(methylsulfonyl) ethyl-3,5-dinitrobenzoate, which can be subsequently converted to the desired diamine monomer 2-methylsulfonylethyl-3,5-diaminobenzoate, which is a known compound, by catalytic hydrogenation. However, its synthesis and utility as a monomer in polymerization have not been reported in literature. Other sulfone-substituted ethyl alcohol derivatives ($R^2$ may be substituted or unsubstituted C1-C7 alkyl groups, or substituted or unsubstituted phenyl groups) may be reacted with 3,5-dinitrobenzoyl chloride (1) or 3,5-dinitrobenzoic acid to prepare the Ester-Sulfonyl diamines (ES-diamines) (4a), as depicted in FIG. 1.

Analogous Amide-Sulfonyl diamine (AS-diamines) (FIG. 1, W=NH or NR$^1$, e.g., compounds 4b-d) may be readily synthesized by reacting sulfone-substituted ethyl amine derivatives (e.g., compounds 2b-d). An exemplary synthetic route to prepare the requisite sulfone-substituted ethylamine derivatives (2b-d) can be realized by exploiting a Michael Addition reaction of R$^1$NH$_2$ to a vinylsulfone (R$^2$SO$_2$CH=CH), or a Michael Addition reaction of R$^1$BnNH (where Bn represents benzyl) to a vinyl sulfone (R$^2$SO$_2$CH=CH), followed by de-benzylation via transfer-hydrogenation with ammonium formate. Because of higher reactivity of primary alkyl amines, benzyl (CH$_2$Ph) is preferably used as a masking group to preclude double Michael addition with two vinyl sulfones. The resulting sulfone-substituted ethyl amines (2b-d) can then be fed into the similar two-step synthesis to obtain AS-diamine monomers (4b-d).

It should be appreciated that the resultant hygromorphic properties and humidity driven motility of any polymer incorporating aryl diamine monomer 4 can be influenced by modification of the polarity of the monomer. Accordingly, increasing the carbon chain lengths of R$^1$ and R$^2$ may reduce the hydrophilicity of the monomer, which thereby reduces the hygromorphic properties (and/or its associated kinetics) of the polymer or copolymer. Conversely, decreasing the chain length of R$^1$ and R$^2$ may increase the hydrophilicity of the monomer, which thereby increases the hygromorphic properties (and/or its associated kinetics) of the polymer or copolymer. Exemplary groups suitable for R$^1$ and R$^2$ include but are not limited to methyl, ethyl, propyl, butyl, pentyl, hexyl, heptyl, benzyl, and phenyl. In accordance with another embodiment of the present invention, R$^1$ and R$^2$ may be substituted with functional groups such as halide, hydroxyl, alkoxyl, acyl, or amido. For example, R$^2$ may be CF$_3$.

The aryl diamine monomer 4 may be incorporated into a variety of polymers and copolymers, including random, block, and tapered polymers. In accordance with an embodiment of the present invention, the aryl diamine monomer 4 is used to provide polyimide, polyamide, and poly(amide-imide) polymers and copolymers, as further described herein.

Figure 2:
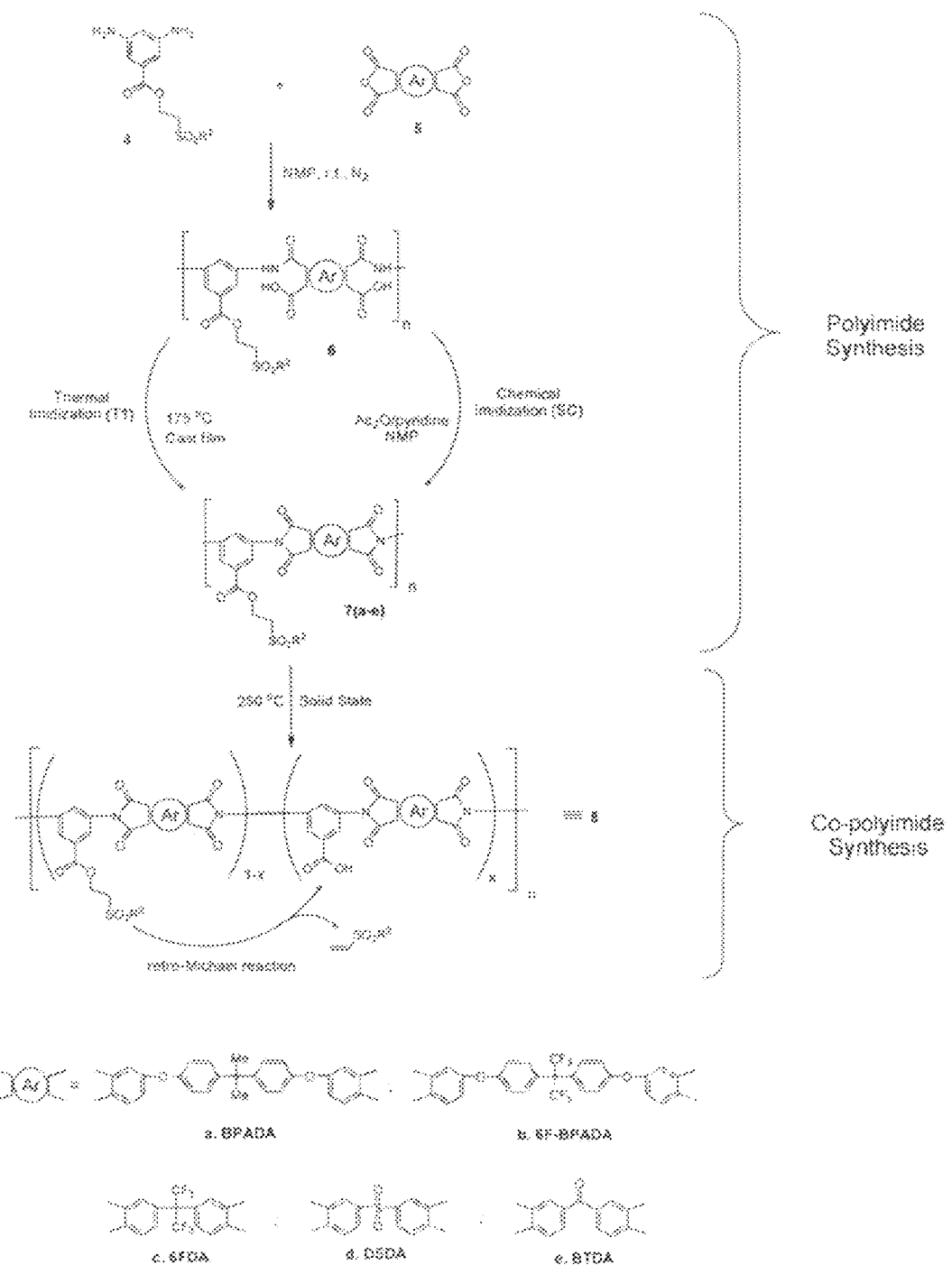
FIG. 2 is a schematic showing a synthetic route for preparing a polyimide and a copolyimide that incorporates the aryl diamine monomer, in accordance with another embodiment of the present invention.

POLYIMIDE: Synthesis of a polyimide is typically accomplished by polymerization of a diamine and a dianhydride in a 1:1 molar ratio to generate a poly(amic acid) precursor, which is then converted to the corresponding polyimide typically by either thermal cure (e.g., by heating to an elevated temperature in solution or solid state) or chemical imidization (e.g., using a dehydrating agent or promoter such as acetic anhydride/triethylamine or acetic anhydride/pyridine). With reference to FIG. 2, an exemplary polyimide synthesis is provided that shows the ester-sulfonyl diamine (ES-diamine) 4a (where W=O) reacted with a dianhydride 5 to form a polyamic acid (PAA) 6, which is converted to a polyimide 7 under suitable imidization conditions.

For example, the ES-diamine 4a can be polymerized with a dianhydride, such as 2,2-[bis(4-phthalic anhydrido)]-1,1,1,3,3,3-hexafluoroisopropane (6FDA); 4,4'-oxybis(phthalic anhydride) (ODPA); 3,3',4,4'-diphenylsulfone tetracarboxylic dianhydride (DSDA); 3,3',4,4'-benzophenone tetracarboxylic dianhydride (BTDA); biphenyltetracarboxylic acid dianhydride (BPDA); 4,4'-(2,2,2-trifluoro-1-phenylethylidene)bis[phthalic anhydride]; 2,2-bis[4-(3,4-dicarboxyphenoxy)phenyl]propane dianhydride (BPADA); 4,4'-(4,4'-Hexafluoroisopropylidenediphenoxy)bis(phthalic anhydride) (6F-BPADA); 4,4'-(p-phenylenedioxy)bis [phthalic anhydride]; 4,4'-(m-phenylenedioxy)bis[phthalic anhydride]; 4,4'-(o-phenylenedioxy)bis[phthalic anhydride]; pyromellitic dianhydride (PMDA); or mixtures thereof. In an embodiment, BPADA, 6F-BPADA, 6FDA, DSDA and BTDA are reacted with the ES-diamine monomer 4a. The ES-diamine 4a and the dianhydride 5 may be reacted in a suitable solvent, such as NMP, to yield a series of polyamic acids (PAA) 6 at room temperature. The PAA's were either thermally imidized at about 175° C. (conditions labelled as "T1" in FIG. 2) or chemically imidized by acetic anhydride and pyridine (conditions labelled as "SC" in FIG. 2) to afford polyimides 7 containing ester-sulfonyl (ES) groups, PI-ES's (7a-e). The IR spectra of polyimides prepared by both methods were observed to be almost identical.

Typically, PAA cast films are thermally imidized at temperatures above about 200° C. However, during the early stage of this work, it was observed that when the PAA 6a cast film was heat-treated at temperatures above 200° C., the corresponding copolymer containing ester-sulfonyl and carboxylic-acid pendants (PEI-ES:A, 8a; FIG. 2) was obtained cleanly from a retro-Michael reaction of the ES pendant group (i.e., —COO—CH$_2$CH$_2$SO$_2$Me), resulting in the formation of COOH-pendant and liberation of methylvinylsulfone molecule. These retro-Michael products were easily detected by $^1$H-NMR experiments after a piece of PEI-ES film had been heated at 250° C. for 2 hr in an NMR tube, followed by adding DMSO-d$_6$ at room temperature (see FIG. 7). Based on the NMR analysis and area-integration results, about 42 mol % of ES groups were found to have converted into carboxylic acids. The new byproduct peaks in spectrum 7b is identical to that of the authentic methylvinylsulfone sample (spectrum 7c). Although about 50% of methylvinylsulfone generated had escaped into air during the heat treatment at 250° C., the other half remained in the polymer film because of the relatively nonvolatile nature of methylvinylsulfone (b.p. 115-120° C./19 torr).

Figure 3:
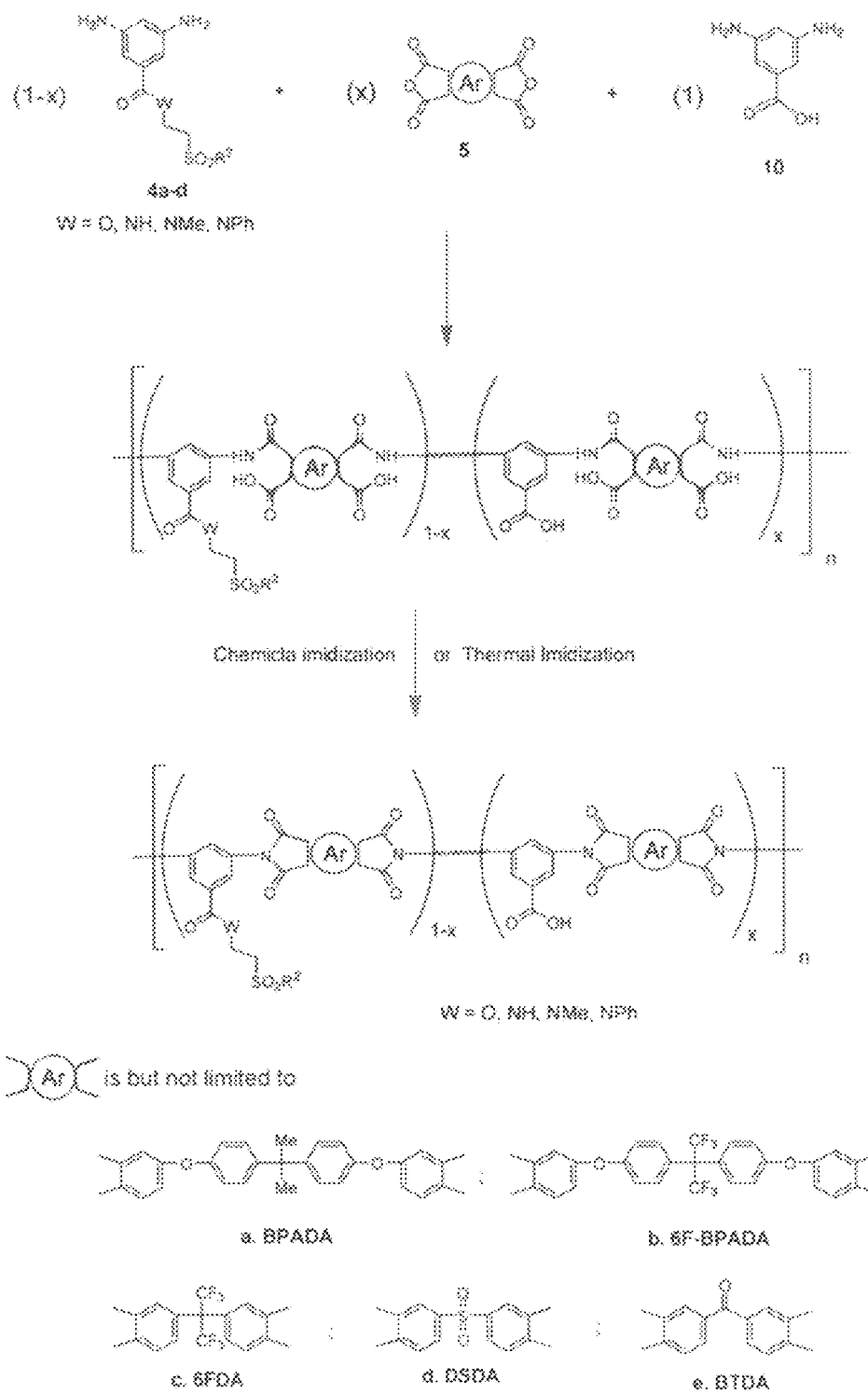
FIG. 3 is a schematic showing copolymerization of the aryl diamine monomer comprising a sulfone moiety and 3,5-diaminoebenzoic acid, with various anhydrides to provide copolyimides, in accordance with another embodiment of the present invention.

Ostensibly, the series of PI-ES:A copolymers can also be prepared by copolymerization with appropriate stoichiometric ratio of the methyl sulfonylethylester-containing diamine (4a), 3,5-diaminobenzoic acid and dianhydride monomer following conventional methods of synthesizing polyimides, i.e., via polyamic acid precursor and chemical or thermal imidization. As depicted in FIG. 3, the scope of such copolymerization can be broadened to include diamines 4b-c, from which the corresponding amide-sulfone pendants could be incorporated as well.

Figure 4:
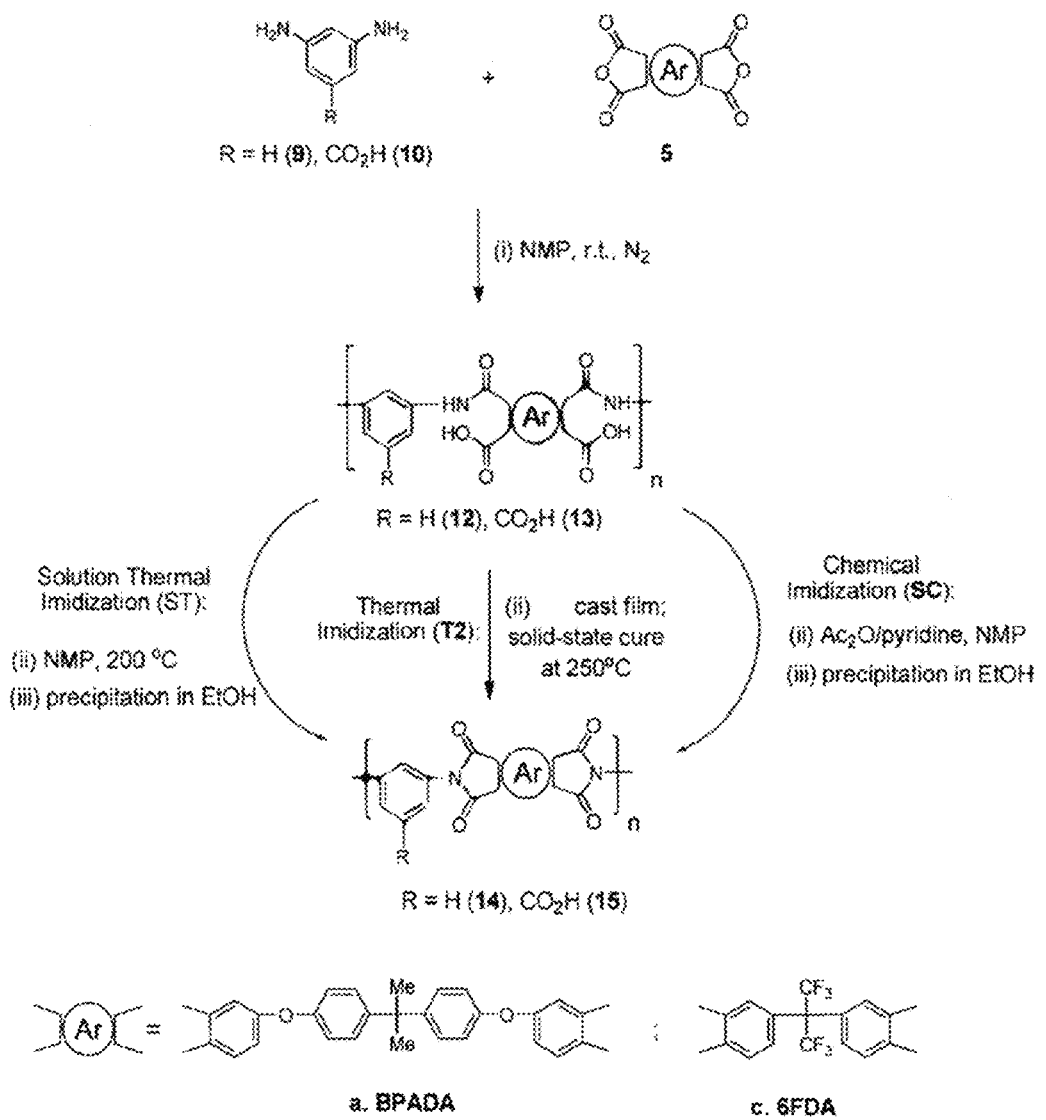
FIG. 4 is a schematic showing a synthetic route for preparing reference or comparative polyimides for comparison with the inventive polymers and copolymers, in accordance with another embodiment of the present invention.

As shown in FIG. 4, comparative materials comprising non-functionalized polyimides (PI-N) (e.g., compounds 14a, c) and polyimides bearing COOH-pendant groups (PI-A) (e.g., compounds 15a,c) were also prepared for comparison purposes by polycondensating m-phenylenediamine (9, m-PDA) and 3,5-diaminobenzoic acid (10, DABA) with BPADA; and 6FDA, respectively to form the respective poly(amic acid)s. Two sets of imidization conditions were used for these less temperature-sensitive polyimides: (ST) solution imidization at 190-200° C.; and (T2) imidization of cast PAA film up to 250° C.

Figure 5:
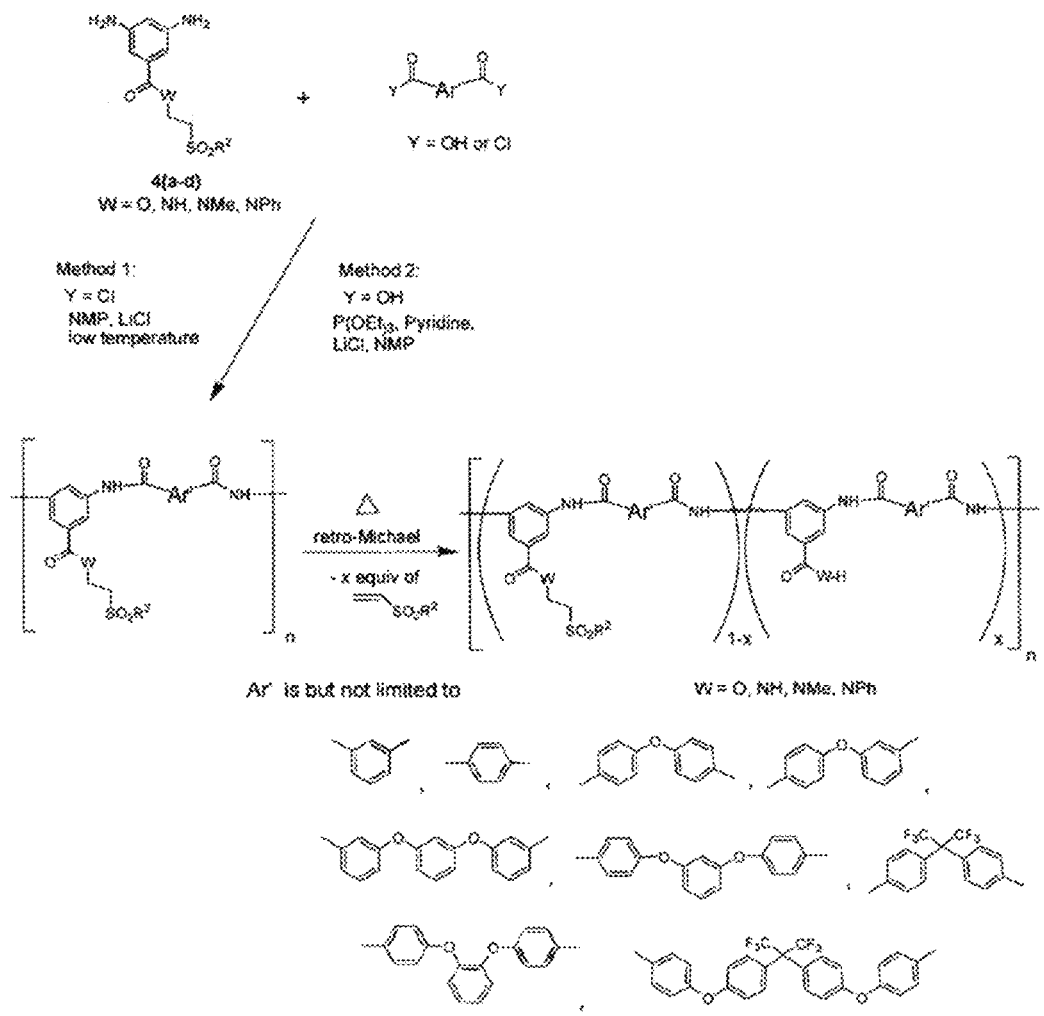
FIG. 5 is a schematic showing a synthetic route for preparing a polyamide and a copolyamide that incorporate the aryl diamine monomer, in accordance with another embodiment of the present invention.

POLYAMIDE: The synthesis of a polyamide is typically accomplished by two general methods. The first method involves polymerization of a diamine and a diacid chloride in a 1:1 molar ratio in an amide solvent such as N,N-dimethylformamide (DMF), N,N-dimethylacetamide (DMAc), N-methylpyrrolidone (NMP), etc. The second method of synthesizing a polyamide involves polymerization of a diamine and a dicarboxylic acid with the aid of a promoter/catalyst combination such as triethylphosphite/pyridine (via Yamazaki-Higashi reaction) in an amide solvent such as N,N-dimethylformamide (DMF), N,N-dimethylacetamide (DMAc), N-methylpyrrolidone (NMP), etc. The preparation of polyamides containing ester-sulfone or amide-sulfone in every repeat unit is depicted in FIG. 5. Also depicted in this figure is the feasibility of converting the resulting amide homopolymers to the corresponding amide copolymers containing in complementary portions of COOH and COWCH$_2$CH$_2$SO$_2$R$^2$ pendants (e.g., where W=O, NH, NMe or NPh) via similar solid-state retro-Michael reaction of the methylsulfonylethyl moieties.

In accordance with an embodiment of the present invention, the dicarboxylic acid monomer may include an aliphatic dicarboxylic acid or an aromatic dicarboxylic acid, or its corresponding diacid halide. Exemplary aliphatic dicarboxylic acids may include, but are not limited to, oxalic acid, malonic acid, succinic acid, glutaric acid, adipic acid, pimelic acid, suberic acid, azelaic acid, dicarboxylic acid compounds or sebacic acid. Aromatic dicarboxylic acids may include, but are not limited to, isophthalic acid; terephthalic acid; 4,4'-dicarboxy biphenyl; 3,3'-dicarboxy biphenyl; 3,3'-diphenyl ether dicarboxylic; 3, 4'-carboxyl diphenyl ether; 4,4'-carboxyl diphenyl ether; 3,3'-carboxyl diphenylmethane; 3,4'-carboxyl diphenylmethane; 4,4'-carboxyl-diphenylmethane; 3,3'-carboxyl diphenyl-difluoro methane: 3,4'-carboxyl-diphenyl-difluoro methane; 4,4'-carboxyl-diphenyl-difluoro methane; 3,3'-carboxyl diphenyl sulfone; 3,4'-carboxyl diphenyl sulfone; 4,4'-dicarboxylic diphenyl sulfone; 3,3'-carboxyl diphenyl sulfide; 3,4'-carboxyl diphenyl sulfide; 4,4'-carboxyl diphenyl sulfide; 3,3'-carboxyl diphenyl ketone; 3,4'-dicarboxylic diphenyl ketone; 4,4'-carboxy-diphenyl ketone; 2,2-bis(3-carboxyphenyl) propane; 2,2-bis(3,4'-dicarboxyphenyl) propane; 2,2-bis(4-carboxyphenyl) propane; 2,2-bis(3-carboxyphenyl) hexafluoropropane; 2,2-bis(3,4'-carboxyphenyl) hexafluoropropane; 2,2-bis(4-carboxyphenyl) hexafluoropropane; 1,3-bis(3-carboxy-phenoxy) benzene; 1,4-bis(3-carboxy-phenoxy) benzene; 1,4-bis (4-carboxy-phenoxy) benzene; 3,3'-(1,4-phenylene-bis(1-methyl-ethylidene)) bis-benzoic acid; 3,4'-(1,4-pbenylene-bis-(1-methyl-ethylidene)) bis-benzoic acid; 4,4'-(1,4-phenylenebis(1-methyl ethylidene)) bis-benzoic acid; 2,2-bis(4-(3-carboxy phenoxy) phenyl) propane; 2,2-bis (4-(4-carboxyphenoxy)phenyl) propane; 2,2-bis (4-(3-carboxy phenoxy) phenyl) hexafluoropropane; 2,2-bis (4-(4-carboxyphenoxy)phenyl) hexafluoropropane; bis (4-(3-carboxy-phenoxy) phenyl) sulfide; bis(4-(4-carboxy phenoxy)phenyl)sulfide; bis(4-(3-carboxyphenoxy) phenyl) sulfone; or bis (4-(4-carboxy phenoxy) phenyl) sulfone. In addition, combinations of two or more may be used.

POLY(AMIDE-IMIDE): There are three common method for the synthesis of a poly(amide-imide) by polymerization of a diamine and: (A) trimellitic anhydride (TMA) with poly(amide-amic acid) as isolable polymer precursor, which can be subsequently either chemically of thermally imidized (see FIG. 6A); (B) a dicarboxylic acid monomer derived from trimellitic anhydride, and aided by triethylphosphite/pyridine (Yamazaki-Higashi reagent) in a 1:1 molar ratio in an amide solvent such as N,N-dimethylformamide (DMF), N,N-dimethylacetamide (DMAc), N-methylpyrrolidone (NMP) etc. (see FIG. 6B); (C) a bis(phthalic anhydride) monomer that can be prepared from low-temperature reaction of 2 equivalents of TMA and a diamine, followed by treatment with acetic anhydride/trimethylamine. Similar to method A, it involves an isolable poly(amide-amic acid) precursor, which can be subsequently either chemically or thermally imidized (see FIG. 6C).

Figure 6A:
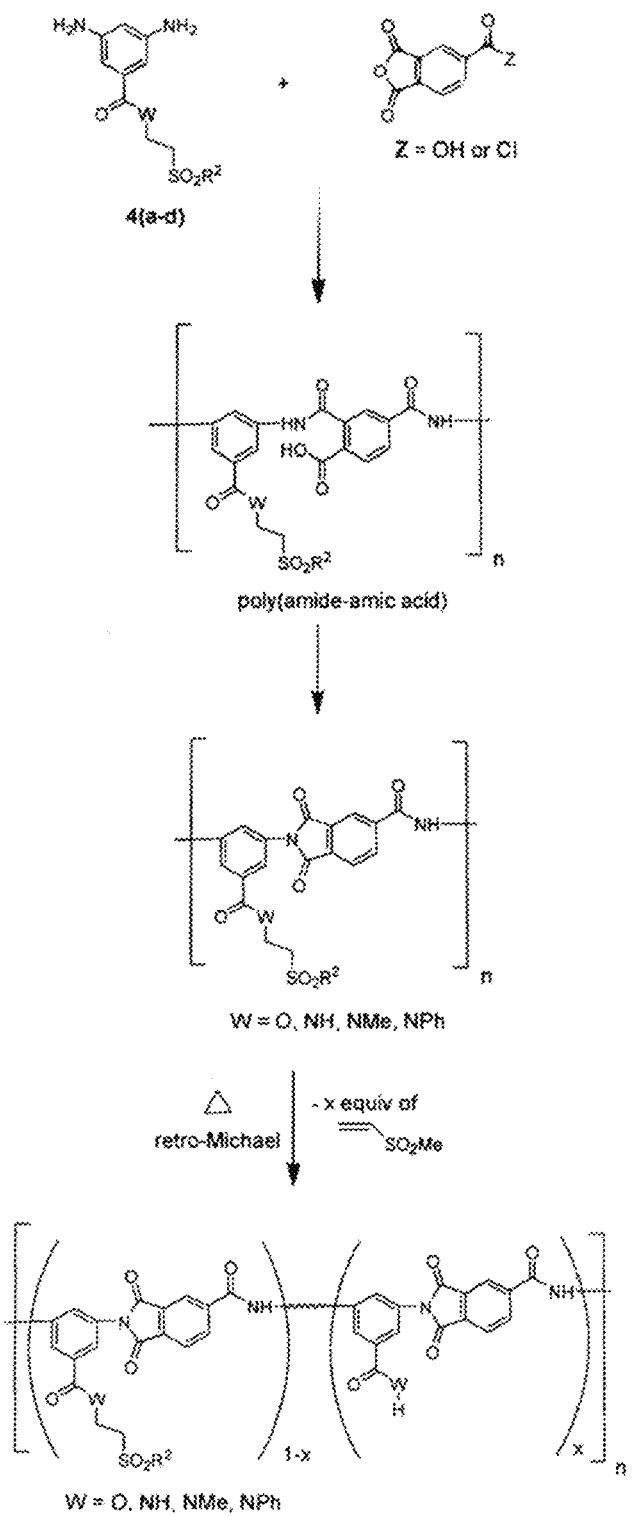
FIG. 6A is schematic showing a first synthetic route for preparing a poly(amide-imide) and copoly(amide-imide) that incorporates the aryl diamine monomer, in accordance with another embodiment of the present invention.
Figure 6B:
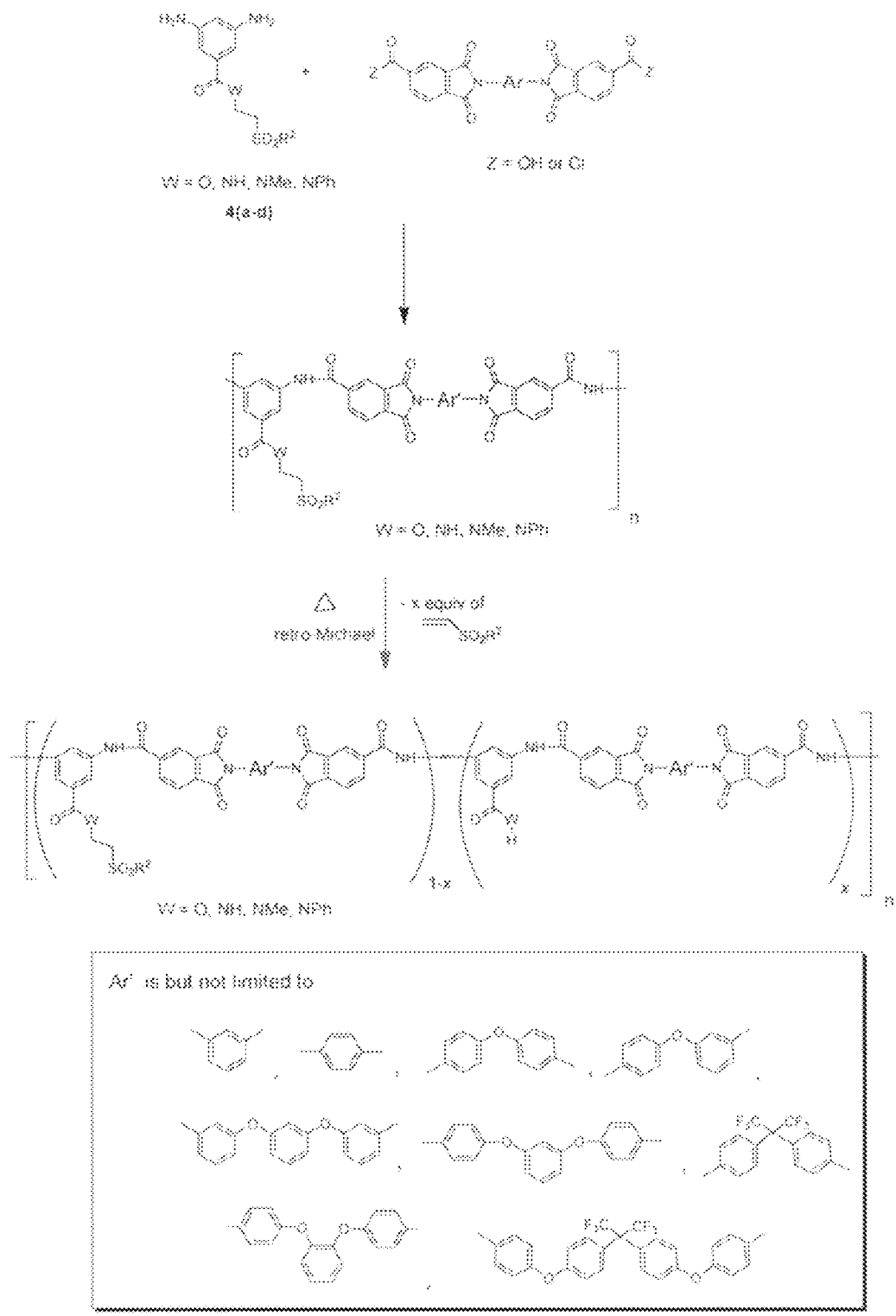
FIG. 6B is schematic showing a second synthetic route for preparing a poly(amide-imide) and copoly(amide-imide) that incorporates the aryl diamine monomer, in accordance with another embodiment of the present invention.
Figure 6C:
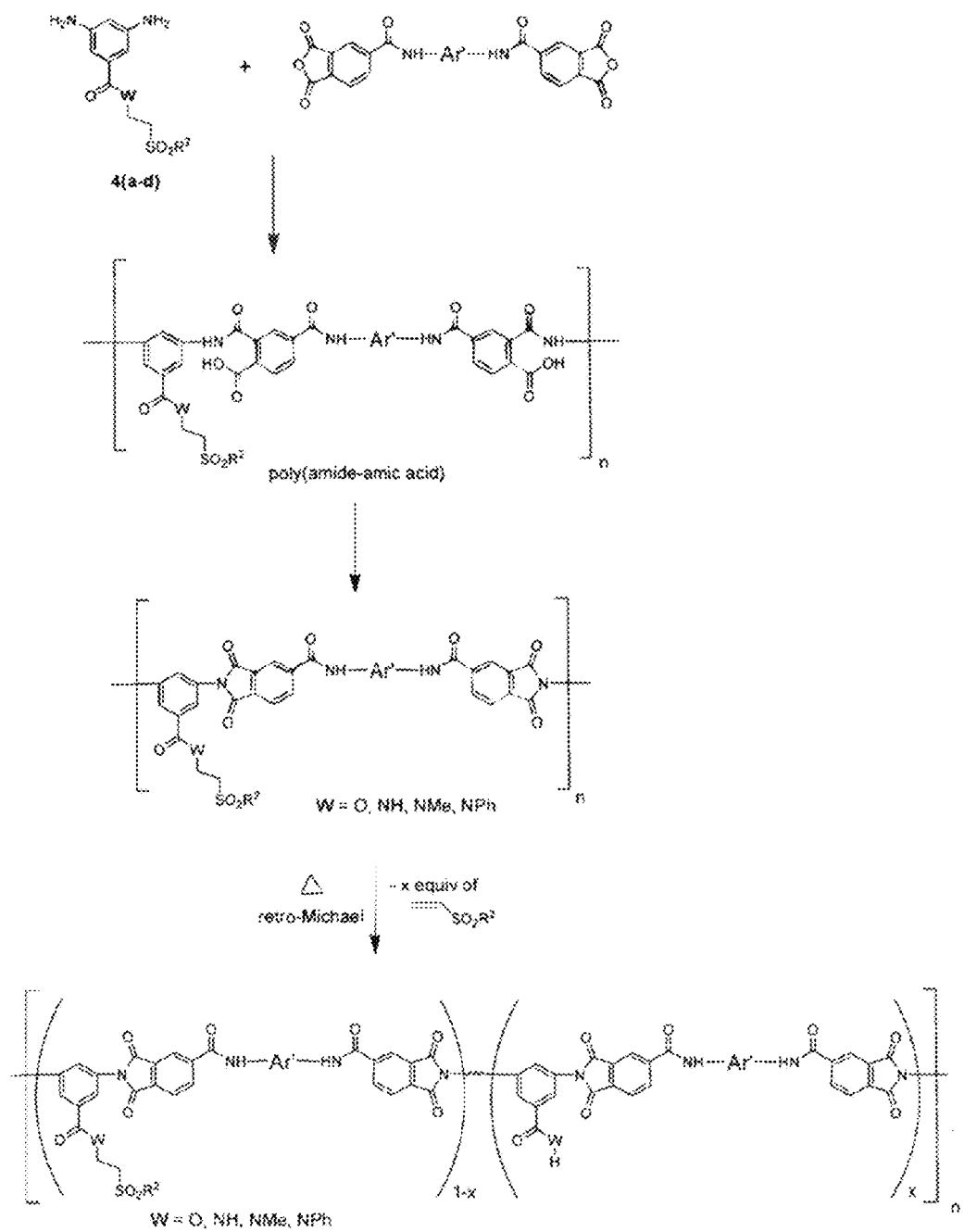
FIG. 6C is schematic showing a third synthetic route for preparing a poly(amide-imide) and copoly(amide-imide) that incorporates the aryl diamine monomer, in accordance with another embodiment of the present invention.

The application of these methods to the aryl diamine monomers 4a-d is depicted in FIGS. 6A, 6B, and 6C. Also depicted in FIGS. 6A-6C is the feasibility of converting the resulting amide homopolymers to the corresponding amide copolymers containing in complementary portions of COOH and COWCH$_2$CH$_2$SO$_2$Me pendants (e.g., where W=O, NH, NMe, or NPh) via similar solid-state retro-Michael reaction of the methylsulfonylethyl moieties.

The following examples and methods are presented as illustrative of the present invention or methods of carrying out the invention, and are not restrictive or limiting of the scope of the invention in any manner.

EXAMPLES

Example 1

2-(Methylsulfonyl)ethyl 3,5-dinitrobenzoate (3a)

Into a 250 mL three-necked, round-bottomed flask equipped with a magnetic stir bar and nitrogen inlet and outlet were placed 3,5-dinitrobenzoyl chloride (1; 8.48 g, 40.0 mmol), 2-(methylsulfonyl)ethanol (2a; 4.96 g, 40 mmol), pyridine (10.0 g), and CH$_2$Cl$_2$ (100 mL). The homogeneous mixture was stirred at room temperature for 24 hrs. The resulting white precipitates were collected by filtration, and recrystallized from ethanol/toluene (1:1) to yield 10.6 g (61%) of white crystals; m.p. 138.5-140.3° C. NMR (DMSO-d$_6$, δ in ppm): 3.11 (s, 3H, CH$_3$), 3.73-3.76 (t, 2H, SO$_2$CH$_2$), 4.76-4.79 (t, 2H, CO$_2$CH$_2$), 8.95-8.96 (d, 2H, Ar—H), 9.04-9.06 (t, 1H, Ar—H). MS (m/z): 318 (M$^+$). Anal. Calcd. for C$_{10}$H$_{10}$N$_2$O$_8$S: C, 37.74%; H, 3.17%; N, 8.80%. Found: C, 37.74%; H, 3.12%; N, 8.90%. ATR-IR (Bulk powder; cm$^{-1}$): 3103, 3027, 3012, 2930, 1730 (C=O), 1632, 1539 (asym.NO$_2$), 1464, 1349 (sym.NO$_2$), 1298 (asym.SO$_2$), 1281, 1195, 1171, 1145, 1131 (sym.SO$_2$), 1079, 1005, 984, 949, 919, 761, 719, 665, 548, 486, 410.

Example 2

2-(Methylsulfonyl)ethyl 3,5-diaminobenzoate (ES-Diamine, 4a)

2-(Methylsulfonyl)ethyl 3,5-dinitrobenzoate (3; 3.18 g, 10.0 mmol) dissolved in THF (50 mL) and palladium on activated carbon (0.20 g) was placed in a hydrogenation bottle. The bottle was tightly secured on a Parr hydrogenation apparatus, flushed four times with hydrogen gas, and pressurized to 55 psi. After the mixture had been agitated at room temperature for 6 hrs under the hydrogen pressure of 55 psi, it was filtered through Celite. The filter cake was washed with THF, and then the filtrate was concentrated on a rotavap to a volume of about 25 mL. The resulting mixture was heated to refluxing, until all the solid dissolved, and allowed to cool to room temperature to afford, after filtration and drying, 2.10 g (81.4%) of white needle crystals; m.p. 113.2-115.5° C. $^1$H NMR (DMSO-d$_6$, δ in ppm): 3.05 (s, 3H, CH$_3$), 3.56-3.59 (t, 2H, SO$_2$CH$_2$), 4.50-4.53 (t, 2H, CO$_2$CH$_2$), 5.00 (s, 4H, NH$_2$), 6.02-6.03 (t, 1H, Ar—H), 6.41-6.42 (d, 2H, Ar—H). MS (m/z): 258 (M$^+$). Anal. Calcd. for C$_{10}$H$_{14}$N$_2$O$_4$S: C, 46.50%, H, 5.46%, N, 10.85%, Found: C, 46.65%, H, 5.39%, N, 10.89%. ATR-IR (Bulk Powder, cm$^{-1}$): 3438, 3416, 3345 (NH$_2$), 3217, 3009, 2995, 2920, 1771 (C=O), 1626, 1596, 1493, 1387, 1355, 1300 (asym.SO$_2$), 1281, 1237, 1194, 1128 (sym.SO$_2$), 1102, 1010, 967, 939, 854, 766, 715, 606.

Example 3

4,4'-(4,4'-Hexafluoroisopropylidenediphenoxy)bis(phthalic anhydride) (6F-BPADA, 5b)

Potassium hydroxide (25 g) was dissolved in 40 g of water in a 250 mL round-bottomed flask fitted with a reflux condenser. Then 2,2-bis[4-(3,4-dicyanophenoxy)phenyl]hexafluoropropane (III; 18.6 g, 30.0 mmol) were added to the solution, followed by 100 mL of methanol. The mixture was refluxed at 105° C. for 40 hrs by which time evolution of ammonia had ceased. The mixture was then diluted with water (300 mL). The acidity was adjusted, by addition of concentrated hydrochloric acid solution, to pH 1.5-2. The resulting precipitate was filtered, washed three times with water and dried to yield 20.0 g (100%) of white powder-4,4'-(4,4'-hexafluoroisopropylidenediphenoxy) bis(phthalic acid) (IV), which was used in next reaction step without further purification. ATR-IR (Bulk powder, cm$^{-1}$: 3100, 2500-3500 (br., COOH), 1849, 1780, 1620, 1592, 1508, 1480, 1277, 1265, 1229, 1213, 1179, 1170, 1158, 1071, 1023, 966, 935, 890, 875, 857, 738, 724, 674, 526, 483.

Then, 4,4'-(4,4'-hexafluoroisopropylidenediphenoxy)bis(phthalic acid) (IV; 19.93 g, 30 mmol) was dissolved in glacial acetic acid (200 mL) and acetic anhydride (150 mL). The mixture was refluxed for 2 hrs until all the solid disappeared. The resulting white needle product, which crystallized on cooling, was filtered to give a 17.8 g (94.4%) of 5b: m.p. 233.0-235.0° C. (ref. 2 233-235° C.). NMR (DMSO-d$_6$, δ in ppm): 7.30-7.32 (d, 4H, Ar—H), 7.50-7.52 (d, 4H, Ar—H), 7.61-7.64 (m, 4H, Ar—H), 8.10-8.12 (d, 2H, Ar—H). ATR-IR (Bulk powder, cm$^{-1}$): 3100, 1848, 1771, 1620, 1591, 1507, 1479, 1277, 1258, 1228, 1207, 1179, 1169, 1157, 1141, 1070, 1023, 973, 965, 953, 929, 888, 874, 856, 843, 757, 737, 707, 673, 647, 633, 543, 482.

Example 4

SC: Representative Procedure for Preparation of PEI-ES Via Solution Chemical Imidization: (7a-SC).

2-(Methylsulfonyl)ethyl 3,5-diaminobenzoate (4a; 0.5166 g, 2.000 mmol) and NMP (8.0 mL) were added to a 25 mL 3-necked flask equipped with a magnetic stirrer, nitrogen inlet and outlet, and stirred under dry nitrogen at room temperature for 30 min. BPADA (5a; 1.041 g, 2.000 mmol) was then charged. The light yellow solution was agitated at room temperature for 24 hrs to afford a viscous poly(amic acid) solution. A mixture of pyridine (0.5 mL) and acetic anhydride (0.5 mL) was added to the solution. Stirring was continued for an additional 24 hrs, and the solution was poured into ethanol to precipitate the polymer product. Fibrous polyimide was collected by filtration, followed by Soxhlet extraction with ethanol for 48 hrs. The polyimide was finally dried overnight in vacuum oven at 100° C. ATR-IR (Fibers, cm$^{-1}$): 3065, 2965, 2930, 1777, 1716, 1620, 1598, 1504, 1477, 1456, 1395, 1350 (asym.SO$_2$), 1265, 1232, 1125 (sym.SO$_2$), 1077, 1013, 846, 764, 742, 626.

Example 5

6FPEI-ES (7b-SC):

2-(Methylsulfonyl)ethyl 3,5-diaminobenzoate (4a; 0.5166 g, 2.000 mmol), 6F-BPADA (5b; 1.257 g, 2.000 mmol) NMP (8.0 mL) were used. ATR-IR (Fibers, cm$^{-1}$): 3070, 2934, 1780, 1724, 1603, 1510, 1478, 1459, 1398, 1355 (asym.SO$_2$), 1261, 1236, 1208, 1175, 1136 (sym.SO$_2$), 1067, 968, 956, 929, 849, 784, 744, 628.

Example 6

6FDI-ES (7c-SC).

2-(Methylsulfonyl)ethyl 3,5-diaminobenzoate (4a; 0.5166 g, 2.000 mmol), 6FDA (5c; 0.889 g, 2.000 mmol), and NMP (8.0 mL) were used. $^1$H NMR (Fibers, DMSO-d$_6$, δ in ppm): 3.06 (s, 3H, CH$_3$), 3.31 (s, 2H, SO$_2$CH$_2$), 4.70 (s, 2H, COOCH$_2$), 7.78 (s, 2H, Ar—H), 7.92 (s, 1H, Ar—H), 7.97 (s, 2H, Ar—H), 8.20 (s, 4H, Ar—H). ATR-IR (Fibers, cm$^{-1}$): 3082, 2932, 1785, 1720, 1600, 1459, 1398, 1353 (asym.SO$_2$), 1297, 1241, 1207, 1190, 1127 (sym.SO$_2$), 1095, 990, 962, 847.

Example 7

DSDI-ES (7d-SC).

2-(Methylsulfonyl)ethyl 3,5-diaminobenzoate (4a; 0.5166 g, 2.000 mmol), DSDA (5d; 0.7165 g, 2.000 mmol) and NMP (8.0 mL) were used. ATR-IR (Fibers, cm$^{-1}$): 3099, 2930, 1784, 1722, 1600, 1554, 1458, 1399, 1360 (conjugated asym.SO$_2$), 1313 (aliphatic asym.SO$_2$), 1287, 1223, 1178, 1147 (conjugated asym.SO$_2$), 1127 (aliphatic asym.SO$_2$), 1100, 1060, 965, 917, 762, 739, 671, 638, 562.

Example 8

BTDI-ES (7e-SC).

2-(Methylsulfonyl)ethyl 3,5-diaminobenzoate (4a; 0.5166 g, 2.000 mmol), BTDA (5c; 0.6444 g, 2.000 mmol) and NMP (8.0 mL) were. The polymer precipitated from solution in 2 hrs after addition of acetic anhydride and trimethylamine due to poor solubility.

Example 9

ST: Representative Procedure for Preparation of PEI-A Via Solution Thermal Imidization: (15a-ST):

3,5-Diaminobenzoic acid (10; 0.761 g, 5.000 mmol) and NMP (12.6 mL) and toluene (5 mL) were added to a 50 mL 3-necked flask equipped with a magnetic stirrer, Dean-Stark trap, nitrogen inlet and outlet, and stirred under dry nitrogen at room temperature for 30 min. BPADA (5a; 2.602 g, 5.000 mmol) was then charged. The light yellow solution was agitated at room temperature for 24 hrs to afford a viscous poly(amic acid) solution. The light yellow solution was agitated and heated to 150° C./1 hr, 160° C./1 hr, 170° C./1 hr, 180° C./1 hr, and 190° C./1 hr to afford a very viscous, gel-like solution. It was diluted by adding NMP (5 mL), allowed to cool to room temperature. The final mixture was poured into ethanol to precipitate a white fibrous solid, which was collected and dried in the oven at 50° C. overnight. The film samples were prepared by dissolving the dried polymer in DMAc with 10 wt % solid contents, cast onto glass slides followed by vacuum evaporation of DMAc at 50° C., and heat-treated at: 100° C./2 hrs, 150° C./2 hrs, 175° C./1 hr, 200° C./1 hr, and 250° C./1 hr. The film thickness was approximately 20-50 μm. ATR-IR (film, cm$^{-1}$): 3067, 2966, 2927, 2500-3500 (br., COOH), 1778, 1715, 1597, 1503, 1476, 1444, 1397, 1348, 1266, 1230, 1172, 1013, 930, 837, 744, 625, 541.

Example 10

6FDI-A (15c-ST):

Following the procedure described for Example 9, 3,5-Diaminobenzoic acid (10; 0.6087 g, 4.000 mmol), 6FDA (5c; 1.777 g, 4.000 mmol), NMP (12.0 mL) and toluene (5 mL) were used. $^1$H NMR (Fibers, DMSO-$d_6$, δ in ppm): 7.77 (s, 2H, Ar—H), 7.84 (s, 1H, Ar—H), 7.93-7.95 (d, 2H, Ar—H), 8.08 (s, 2H, Ar—H), 8.18-8.20 (d, 2H, Ar—H), 13.43 (br. s, 1H, COOH). ATR-IR (Fibers, cm$^{-1}$): 3091, 2500-3500 (br., COOH), 1784, 1718, 1596, 1452, 1399, 1350, 1298, 1240, 1206, 1188, 1086, 990, 964, 846, 717, 631.

Example 11

T1: Representative Procedure for Preparation of PEI-ES (7a-T1):

2-(Methylsulfonyl)ethyl 3,5-diaminobenzoate (4a; 0.5166 g, 2.000 mmol) and NMP (8.0 mL) were added to a 25 mL 3-necked round-bottomed flask equipped with a magnetic stirrer, nitrogen inlet and outlet, and stirred under dry nitrogen at room temperature for 30 min. BPADA (5a; 1.041 g, 2.000 mmol) was then charged. The light yellow solution was agitated at room temperature for 24 hrs to afford a viscous poly(amic acid) solution. This solution was poured into a glass dish, followed by vacuum evaporation of NMP at 50° C., and heat-treated at: 100° C./2 hrs, 150° C./2 hrs, and 175° C./1 hr to form imidized polymers. The film thickness was approximately 20-50 μm. ATR-IR (Film, cm$^{-1}$): 3065, 2967, 2930, 1777 $\nu_{sym}$ (imide CO), 1715 $\nu_{sym}$ (imide CO), 1597, 1503, 1477, 1444, 1396, 1350, 1265, 1231, 1119, 1076, 1013, 838, 741.

Example 12

6FPEI-ES (7b-T1):

Following the procedure described for Example 11, 2-(Methylsulfonyl)ethyl 3,5-diaminobenzoate (4a; 0.5166 g, 2.000 mmol), 6F-BPADA (5b; 1.257 g, 2.000 mmol) and NMP (8.0 mL) were used. ATR-IR (Film, cm$^{-1}$): 3070, 2934, 1780, 1724, 1603, 1510, 1478, 1459, 1398, 1355, 1261, 1236, 1208, 1175, 1136, 1067, 968, 956, 929, 849, 784, 744, 628.

Example 13

6FDI-ES (7c-T1):

Following the procedure described for Example 11, 2-(Methylsulfonyl)ethyl 3,5-diaminobenzoate (4a; 0.5166 g, 2.000 mmol), 6FDA (5c; 0.889 g, 2.000 mmol) and NMP (8.0 mL) were used. $^1$H NMR (Fibers, DMSO-$d_6$, δ in ppm): 3.06 (s, 3H, CH$_3$), 3.64 (s, 2H, SO$_2$CH$_2$), 4.69 (s, 2H, COOCH$_2$), 7.28-7.31 (d, 4H, Ar—H), 7.48-7.59 (m, 8H, Ar—H), 7.90 (s, 1H, Ar—H), 8.02-8.04 (d, 2H, Ar—H), 8.17 (s, 2H, Ar—H). ATR-IR (Film, cm$^{-1}$): 3082, 2932, 1785, 1720, 1600, 1459, 1398, 1353, 1297, 1241, 1207, 1190, 1127, 1095, 990, 962, 847.

Example 14

DSDI-ES (7d-T1):

Following the procedure described for Example 11, 2-(Methylsulfonyl)ethyl 3,5-diaminobenzoate (4a; 0.5166 g, 2.000 mmol), DSDA (5d; 0.7165 g, 2.000 mmol), and NMP (8.0 mL) were used. ATR-IR (Film, cm$^{-1}$: 3094, 2930, 1783, 1716, 1597, 1456, 1396, 1366, 1311, 1283, 1221, 1176, 1176, 1124, 1095, 1057, 1006, 963, 914, 855, 761, 737, 669, 635, 557.

Example 15

BTDI-ES (7e-T1):

Following the procedure described for Example 11, 2-(Methylsulfonyl)ethyl 3,5-diaminobenzoate (4a; 0.5166 g, 2.000 mmol), BTDA (5e; 0.6444 g, 2.000 mmol), and NMP (8.0 mL) were used. ATR-IR (Film, cm$^{-1}$: 3093, 2930, 1779, 1713, 1595, 1455, 1396, 1354, 1288, 1248, 1195, 1125, 1090, 959, 921, 853, 768, 714, 631.

Example 16

PEI-ES: A Copolymers Via Solid-State Thermal Imidization and Retro-Michael Reaction:

2-(Methylsulfonyl)ethyl 3,5-diaminobenzoate (4a; 0.5166 g, 2.000 mmol) and NMP (8.0 mL) were added to a 25 mL 3-necked round-bottomed flask equipped with a magnetic stirrer, nitrogen inlet and outlet, and stirred under dry nitrogen at room temperature for 30 min. BPADA (5a; 1.041 g, 2.000 mmol) was then charged. The light yellow solution was agitated at room temperature for 24 hrs to afford a viscous poly(amic acid) solution. This solution was poured into a glass dish, followed by vacuum evaporation of NMP at 50° C., and heat-treated at: 100° C./2 hrs, 150° C./2 hrs, 175° C./1 hr, 200° C./1 hr, and 250° C./1-16 hrs to form a series of imidized copolymers of PEI-ES and PEI-A. Retro-Michael reaction of the methylsulfonylethyl ester pendant and late-stage of imidization of amic acid moiety occurred concurrently at temperatures greater than 175° C. The resulting copolyimides are designated as PEI-ES:A-x hr, where x corresponds to number of hours at 250° C. and qualitatively correlated to the amount of CO$_2$H pendants generated. The film thickness was approximately 20-50 μm. ATR-IR (Film, cm$^{-1}$) for PEI-ES:A-4 hr: 3086, 2500-3500 (br., COOH), 1785, 1718, 1600, 1458, 1399, 1361 (asym SO$_2$), 1298, 1240, 1206, 1189 (sym SO$_2$), 1148, 1090, 989, 963, 846, 741, 718, 631, 568.

Figure 7:
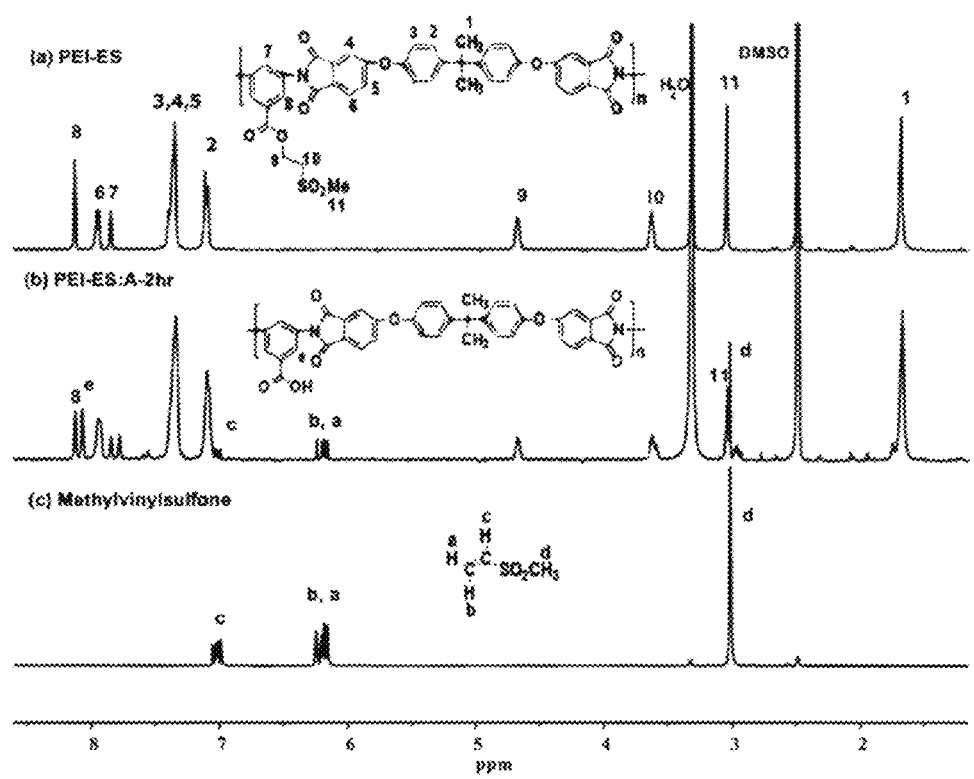
FIG. 7 shows three $^1$H-NMR spectra and peak assignments of (a) an exemplary polyimide (i.e., PEI-ES, compound 7a); (b) PEI-ES after heating at 250° C./N$_2$ for 2 hrs, resulting in the partial formation of PEI-A (structure shown) and methylvinylsulfone; and (c) a commercial sample of methylvinylsulfone, in accordance with another embodiment of the present invention.

With reference to FIG. 7, $^1$H-NMR spectra and peak assignments of PEI-ES are provided showing: (a), PEI-ES after heated at 250° C./N$_2$ for 2 hrs (b), and commercial sample of methylvinylsulfone (c) for authentication. All spectra were taken in DMSO-$d_6$, which has protio residues with signals at 3.38 ppm (H$_2$O) and 2.50 ppm (DMSO). Based on area integration (A) of the pertinent peaks numerically or alphabetically labeled in spectrum 2(b), about 42 mol % of PEI-ES was found to have decomposed into PEI-A as calculated form the following equation, [$A_e/(A_e+A_8)$]×100%; and about 50 mol % loss of methylvinylsulfone formed as calculated form the following equation, (1−$A_{a,b}$/$A_e$)×100%; where $A_i$ is the area of the corresponding peak i.

Example 17

PEI-A (15a-T2):

Following the polymerization procedure and imidization conditions described for PEI-ES:A (Example 16), 3,5-Diaminobenzoic acid (10; 0.761 g, 5.000 mmol), BPADA (5a; 2.602 g, 5.000 mmol) and NMP (12.6 mL) were used. ATR-IR (film, cm$^{-1}$): 3067, 2966, 2927, 2500-3500 (br., COOH), 1778, 1715, 1597, 1503, 1476, 1444, 1397, 1348, 1266, 1230, 1172, 1013, 930, 837, 744, 625, 541.

Example 18

6FPI-A (15c-T2):
Following the polymerization procedure and imidization conditions described for PEI-ES:A (Example 16), 3,5-Diaminobenzoic acid (10; 0.6087 g, 4.000 mmol), 6FDA (5c; 1.777 g, 4.000 mmol) and NMP (12.0 mL) were used. ATR-IR (fibers, cm$^{-1}$): 3091, 2500-3500 (br., COOH), 1784, 1718, 1596, 1498, 1399, 1350, 1298, 1240, 1206, 1188, 1140, 1086, 990, 964, 846, 744, 717, 645.

Example 19

PEI-N (Ultem®-1000, 14a-T2):
Following the polymerization procedure and imidization conditions described for PEI-ES:A (Example 16), 3,5-Diaminobenzene (9; 0.2162 g, 2.000 mmol), BPADA (5a; 0.889 g, 2.000 mmol), and NMP (10.0 mL) were used were used. ATR-IR (film, cm$^{-1}$): 3081, 1784, 1719, 1625, 1603, 1495, 1456, 1437, 1353, 1297, 1240, 1206, 1189, 1140, 1100, 1005, 985, 891, 846, 786, 755, 717, 679, 629, 569, 545.

Example 20

6FDI-N (14c-T2):
Following the polymerization procedure and imidization conditions described for PEI-ES:A (Example 16), 3,5-Diaminobenzene (9; 0.2162 g, 2.000 mmol), 6FDA (5c; 1.041 g, 2.000 mmol) and NMP (10.0 mL) were used. ATR-IR (film, cm$^{-1}$): 3066, 2966, 2873, 1777, 1716, 1619, 1599, 1495, 1476, 1444, 1350, 1265, 1233, 1172, 1100, 1072, 1013, 920, 837, 776, 741, 682, 624, 543.

Example 21

Ultem®-1000 Cast Films:
Cast films of commercial Ultem®-1000 were prepared from either chloroform or DMAc solution (10 w/v %), and similarly dried prior to characterization experiments.

Figure 8:
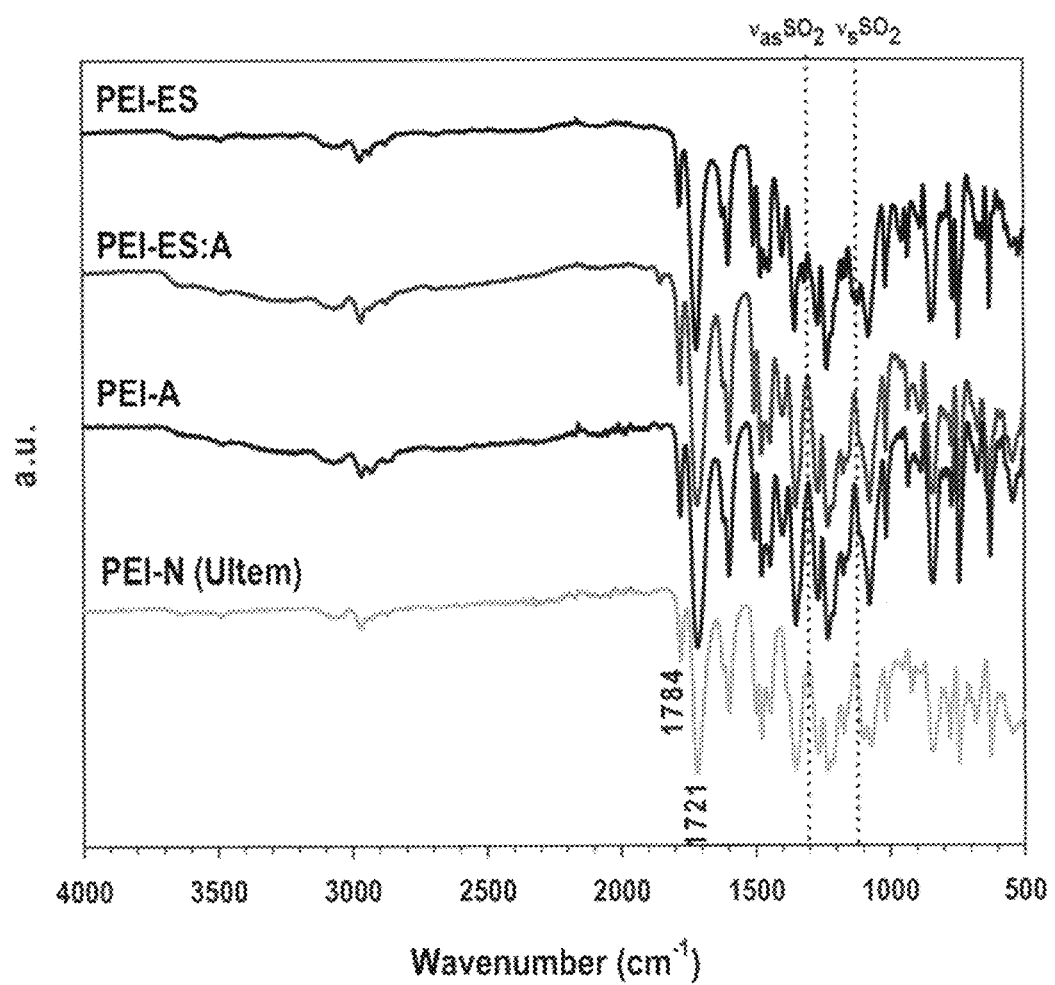
FIG. 8 shows IR spectra comparing four polyimides, i.e., PEI-ES (compound 7a); PEI-ES:A-4 hr (example 24); PEI-A (compound 15); and PEI-N (Ultem® 1000), in accordance with another embodiment of the present invention.

With reference to FIG. 8, IR spectra of PEI-ES, PEI-ES:A-4 hr, PEI-A and PEI-N (Ultem) are provided. The $v_{asym}$ SO$_2$ (about 1350 cm$^{-1}$) and $v_{sym}$ SO$_2$ (about 1130 cm$^{-1}$) stretches are present in PEI-ES, are obscured by nearby strong bands in PEI-ES:A-4 hr, and are absent in both PEI-A and PEI-N (Ultem) samples.

Figure 9A:
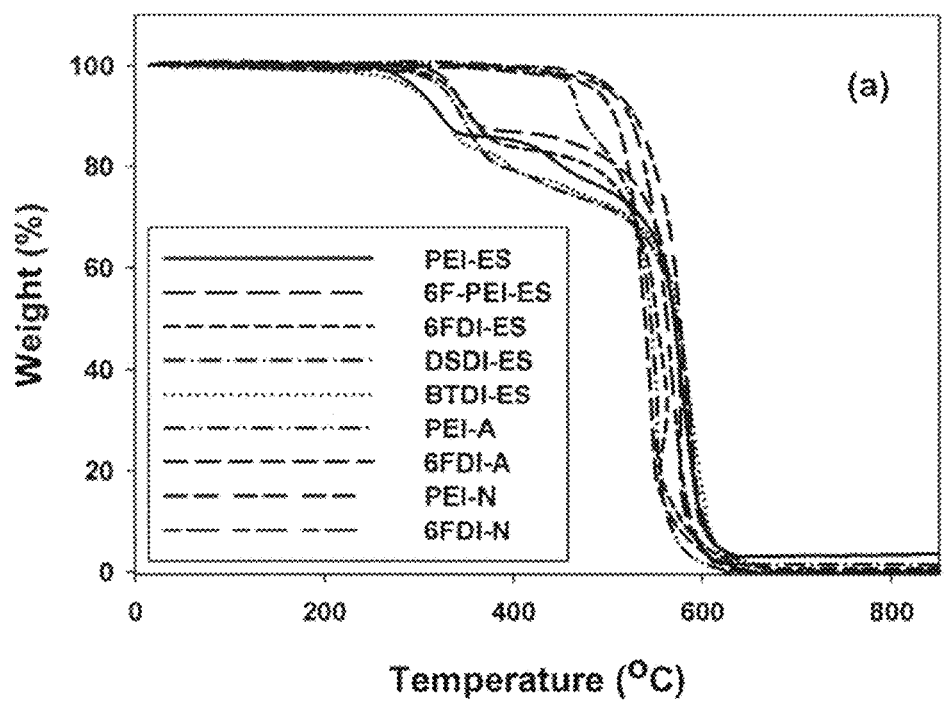
FIGS. 9a and 9b show TGA thermograms of PI-ES, PI-A and PI-N samples (a) in air and (b) in N$_2$, respectively, in accordance with another embodiment of the present invention.

With reference to FIG. 9, thermogravimetric analysis (TGA) thermograms of PI-ES, PI-A and PI-N samples (a) in air and (b) in N$_2$.

Figure 10:
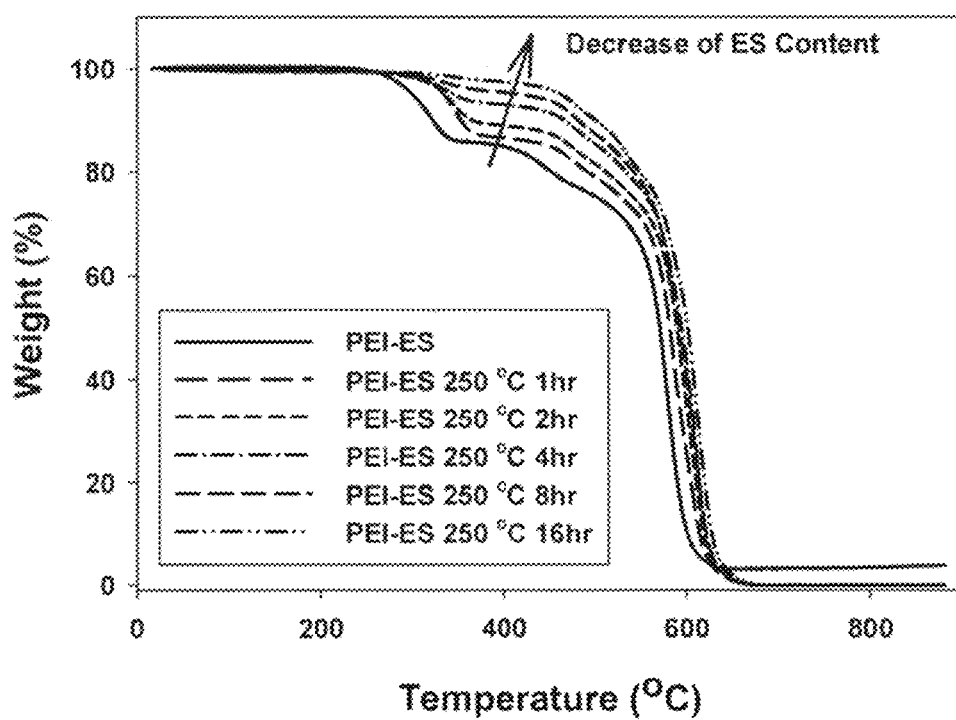
FIG. 10 shows TGA thermograms of PEI-ES (compound 7a) and PEI-ES:A-xhr samples in air (example 24), in accordance with another embodiment of the present invention.
Figure 11:
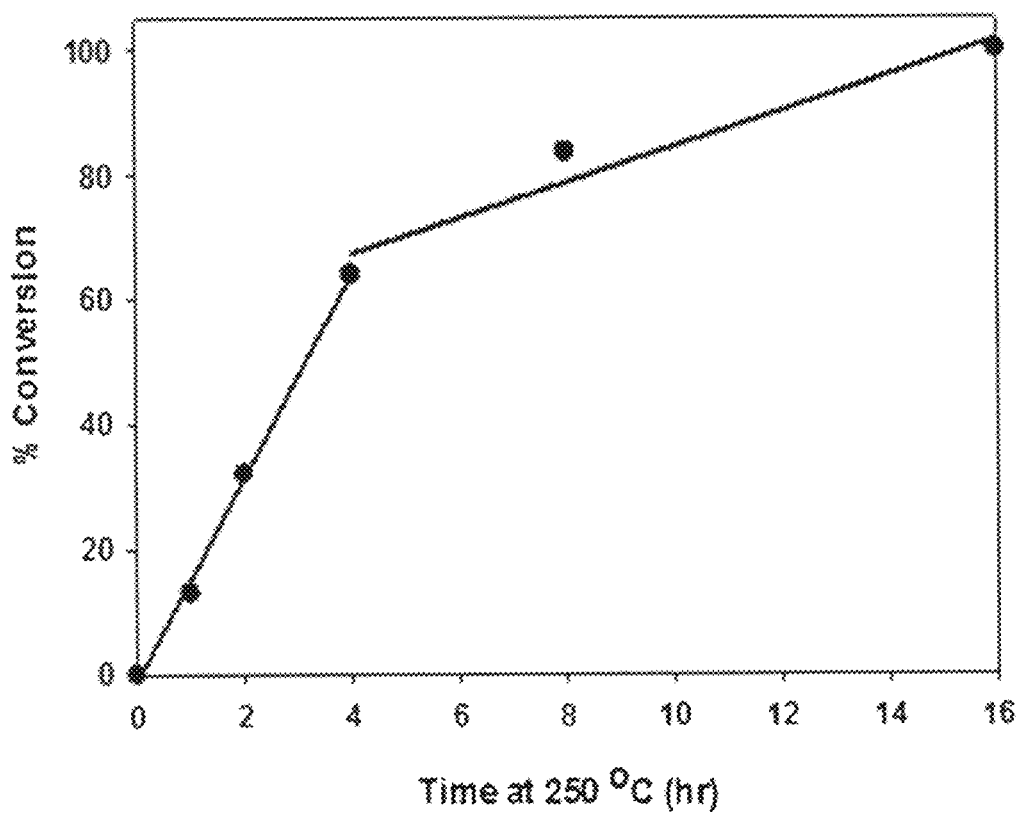
FIG. 11 shows TGA monitoring of retro-Michael reaction by following the ester-sulfonyl to carboxylic-acid conversion after the respective PEI-ES samples had been heated at 250° C. for the predetermined durations.

With reference to FIG. 10, TGA thermograms of PEI-ES and PEI-ES:A-xhr samples in air. The extent of retro-Michael reaction that varies with heating time at 250° C. is determined by is determined by calculating the percentage of weight increase at 400° C., i.e., ES→A Conversion %=(Weight %$_{PEI-A}$−Weight %$_{PEI-ES:A}$)/(Weight %$_{PEI-A}$−Weight %$_{PEI-ES}$). With reference to FIG. 11, TGA monitoring of retro-Michael reaction by following the ester-sulfonyl→carboxylic-acid conversion after the respective PEI-ES samples had been heated at 250° C. for the predetermined durations.

Example 22

TABLE 1

Various properties of polyimide films.

| Sample | Diamine | Dianhydride | T$_g$$^a$ | T$_g$$^b$ | T$_{d5\%}$$^c$ in air | T$_{d5\%}$$^c$ in N$_2$ | E$^d$ (GPa) | Water Abs.$^e$ |
|---|---|---|---|---|---|---|---|---|
| PEI-ES (7a) | ES-Diamine | BPADA | 193 | 221 | 282 | 300 | 1.38 ± 0.14 | 2.24 ± 0.05 |
| 6F-PEI-ES (7b) | ES-Diamine | 6F-BPADA | 221 | 231 | 321 | 335 | 1.07 ± 0.10 | 2.39 ± 0.08 |
| 6FDI-ES (7c) | ES-Diamine | 6FDA | 254 | UD$^f$ | 313 | 322 | 1.27 ± 0.24 | 2.31 ± 0.11 |
| DSDI-ES (7d) | ES-Diamine | DSDA | UD$^f$ | UD$^f$ | 297 | 302 | 1.75 ± 0.16 | 4.81 ± 0.07 |
| BTDI-ES (7e) | ES-Diamine | BTDA | UD$^f$ | UD$^f$ | 284 | 292 | 2.15 ± 0.25 | 4.86 ± 0.21 |
| PEI-N (14a) | m-PDA | BPADA | 217 | 247 | 502 | 513 | 2.68 ± 0.18 | 1.23 ± 0.06 |
| Ultem (14a) | m-PDA | BPADA | 217 | 248 | 504 | 509 | 2.74 ± 0.19 | 1.22 ± 0.04 |
| 6FDI-N (14c) | m-PDA | 6FDA | 280 | 307 | 492 | 497 | 1.67 ± 0.23 | 1.31 ± 0.03 |
| PEI-A (15a) | m-DABA | BPADA | 249 | 273 | 441 | 443 | 3.08 ± 0.28 | 2.86 ± 0.12 |
| 6FDI-A (15c) | m-DABA | 6FDA | 278 | 296 | 459 | 464 | 2.13 ± 0.13 | 4.81 ± 0.10 |
| CP2$^g$ | APB | 6FDA | 199 | 219 | 526 | 530 | 1.9 ± 0.15 | 0.93 ± 0.12 |

(a) T$_g$ measured from inflection in baseline on DSC thermogram obtained in N$_2$ with a heating rate of 10° C./min, reported in ° C. For samples 7a-7e, first scan was run to 200° C., cooling to room temp followed by rescanning to 300° C. For all other samples, both initial scan and rescan were run to 350° C.; (b) T$_g$ measured from the peak of tan delta (DMA) as an average value taken from 3 measurements, reported in ° C.; (c) Temperature at which 5% weight loss recorded on TGA thermogram obtained with a heating rate of 10° C./min, reported in ° C.; (d) Modulus determined in tension mode at 25° C. as an average value taken from 3 specimens per sample; (e) Weight percentage (Wt %) increase after films were immersed in distilled water for 2 days; (f) UD=T$_g$ undetected below 300° C.; retro-Michael addition and decarboxylation are likely to have occurred above 300° C. for these polyimides; (g) Ref. 23(a), CP2 structure:

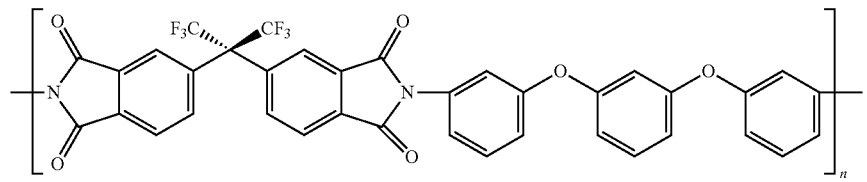

Example 23

TABLE 2

Polymerization and Imidization conditions, polyimide molecular weights, polydispersity, and film quality.

| Sample | Step 1 Solvent | Step 2 | $M_n{}^a$ | $M_w{}^a$ | $PDI^a$ | Film Quality |
|---|---|---|---|---|---|---|
| 6F-PEI-ES(7b) | NMP | $SC^b$ | 15,450 | 41,500 | 2.67 | Tough, creasable |
| 6F-PEI-ES (7b) | NMP | $T1^c$ | 7,070 | 29,100 | 4.12 | Brittle |
| 6FDI-ES(7c) | NMP | $SC^b$ | 14,300 | 58,500 | 4.09 | Tough, creasable |
| 6FDI-ES(7c) | NMP | $T1^c$ | 5,410 | 17,800 | 3.30 | Brittle |
| 6FDI-ES(7c) | DMAc | $SC^b$ | 19,900 | 59,400 | 2.98 | Tough, creasable |
| 6FDI-ES(7c) | DMAc | $T1^c$ | 6,240 | 18,900 | 3.03 | Brittle |
| 6FDI-A-T1(15c) | NMP | $T1^c$ | 8,820 | 26,600 | 3.02 | Brittle |
| 6FDI-A-T2(15c) | NMP | $ST^c$ | 17,900 | 83,300 | 4.66 | Tough, creasable | a. Number-average molecular weight ($M_n$), weight-average molecular weight ($M_w$), and polydispersity determined using GPC in THF at 30.0° C. with polystyrene standard; b. SC: Solution chemical imidization at room temperature; c. T1: thermal imidization of cast PAA films at 175° C.; d. ST: one-pot, solution thermal imidization at 190-200° C.

Example 24

TABLE 3

Thermal and mechanical properties of thermally derived copolyimide films.

| Sample | Conver.$^a$ (%) | $T_g{}^b$ | $T_{d5\%}{}^c$ | $T_{d5\%}{}^d$ | $E'^e$ (GPa) | Density$^f$ (g/cm$^3$) |
|---|---|---|---|---|---|---|
| PEI-ES (7a) | 0 | 221 | 282 | 300 | 1.38 ± 0.14 | 1.332 ± 0.003 |
| PEI-ES:A-1 hr$^g$ | 13.0 | 247 | 334 | 342 | 1.86 ± 0.24 | 1.326 ± 0.004 |
| PEI-ES:A-2 hr$^g$ | 32.1 | 267 | 337 | 343 | 1.30 ± 0.12 | ND$^h$ |
| PEI-ES:A-4 hr$^g$ | 64.1 | 279 | 345 | 361 | 1.28 ± 0.17 | ND$^h$ |
| PEI-ES:A-8 hr$^g$ | 83.5 | 286 | 417 | 429 | 1.27 ± 0.15 | ND$^h$ |
| PEI-ES:A-16 hr$^g$ | 100 | 287 | 463 | 472 | 1.31 ± 0.22 | 1.323 ± 0.005 |
| PEI-A (12a) | 100 | 273 | 441 | 443 | 3.08 ± 0.28 | 1.320 ± 0.003 |
| PEI-N (15a) | — | 247 | 502 | 513 | 2.68 ± 0.19 | 1.271 ± 0.007 |

Notes: (a) Percentage of carboxylic acid converted from ester-sulfonyl groups or present in polymer; (b) $T_g$ measured from the peak of tan delta (DMA) as an average value taken from 3 measurements, reported in ° C.; (c) Temperature at which 5% weight loss recorded on TGA thermogram obtained with a heating rate of 10° C./min in air, reported in ° C.; (d) Temperature at which 5% weight loss recorded on TGA thermogram obtained with a heating rate of 10° C./min in air, reported in ° C.; (e) Modulus determined in tension mode at 25° C. as an average value taken from 3 specimens per sample; (f) Density was measured by floating the samples in CCl$_4$/Methanol mixture. A 5.00 mL of the mixture was drawn by a pipette and weighed. An average value was taken from 3 measurements; (g) PEI-EA films were heated at 250° C. for 1-16 hrs under N$_2$ to yield PEI-ES:A copolymers via retro-Michael reaction; (h) Not determined (ND).

Example 25

TABLE 4

Solubility testing of polyimide samples.

| Sample | EtOH | ACE | DCM | CHCl$_3$ | THF | DMSO | DMAc | NMP |
|---|---|---|---|---|---|---|---|---|
| PEI-ES (7a) | – | – | + | + | – | + | + | + |
| 6F-PEI-ES (7b) | – | +/– | + | + | + | + | + | + |
| 6FDI-ES (7c) | – | +/– | + | + | + | + | + | + |
| DSDI-ES (7d) | – | – | – | – | – | + | + | + |
| BTDI-ES (7e) | – | – | – | – | – | – | – | – |
| PEI-N (14a) | – | – | – | + | – | + | + | + |
| Ultem (14a) | – | – | + | + | – | + | + | + |
| 6FDI-N (14c) | – | – | + | – | – | + | + | + |
| PEI-A (15a) | – | + | – | – | + | + | + | + |
| 6FDI-A (15c) | – | + | – | – | + | + | + | + |

EtOH is ethanol; ACE is acetone; DCM is dichloromethane; THF is tetrahydrofuran; DMSO is dimethylsulfoxide; DMAc is dimethylacetamide; NMP is N-methylpyrrolidinone; solubility designations are +: Soluble; –: Insoluble; +/–: Partially soluble.

Thermal and Mechanical Properties:

The glass transition temperatures (T$_g$'s) were determined by both DSC and DMA techniques. T$_g$'s were measured from inflection in baseline on DSC thermograms and from the peak of tan δ (DMA), respectively. Generally, the T$_g$'s values from DMA are higher than the DSC values (see Table 1 as Example 22). Of the three types of polyimides and given the same dianhydride, the "ES" series exhibit the lowest T$_g$'s, most probably due to the plasticizing effect of ES groups, and PI-A's show the highest T$_g$'s because of the inter-chain hydrogen bonding of carboxylic acids. Derived from the most rigid dianhydride, the glass transition of BTDI-ES was undetected below 300° C., and the degradation of the polymer started just slightly above 300° C. The T$_g$'s of the other members of "-ES" are 193-279° C. according to the DSC results, and 221-291° C. by DMA experiments. On the whole, the T$_g$ of the "ES" series increased with increasing rigidity of dianhydride monomers, BTDI>DSDI>6FDI>6F-PEI>PEI, in agreement with the trend observed for other structurally similar polyimides.

Figure 9B:
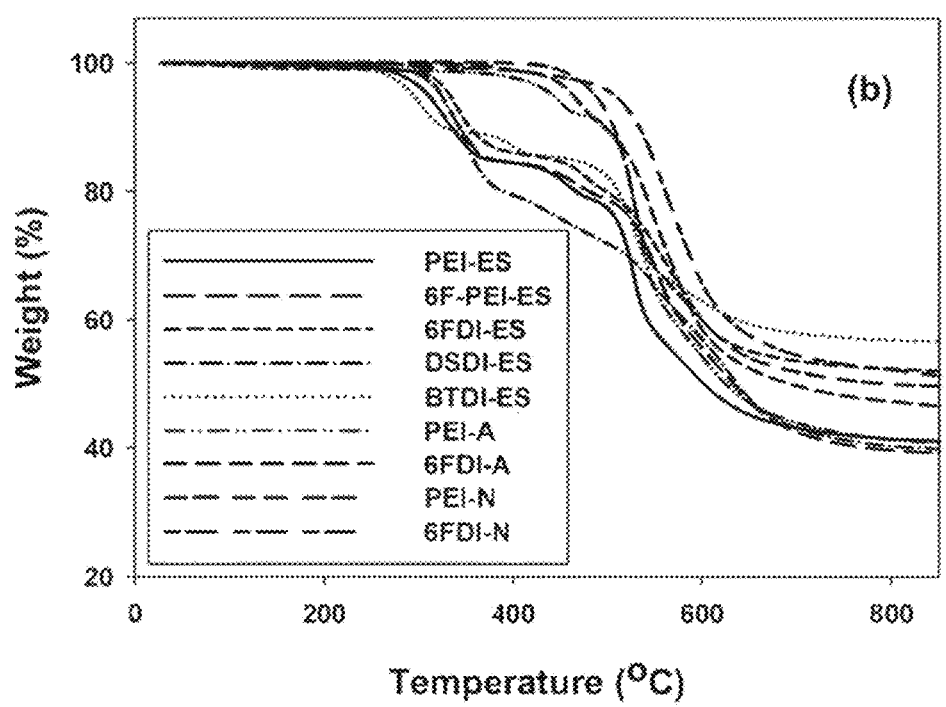

The thermal stability was evaluated by TGA. As expected, the PI-ES samples showed the lowest thermal stability due to the aliphatic ES side chains. They all exhibited a two-stage degradation process (see FIGS. 9A-9B). Their 5 wt % degradation temperatures are in the range of 282-321° C. in air (FIG. 9A) and 292-335° C. in N$_2$ (FIG. 9B). The non-functional PEI-N (Ultem®) and 6FDI-N exhibited the best thermal and thermos-oxidative stabilities. Their 5 wt % degradation temperatures are in the range of 492-504° C. in air and 497-509° C. in N$_2$ (see FIG. 10). The PI-A samples showed lower thermal stability than PI-N's since the carboxylic groups underwent decarboxylation above 300° C.

The thermomechanical properties of the polyimide films were characterized by DMA to confirm the expected trends (Table 1 as Example 22). For "ES" series, the films of the most rigid BTDI-ES have the largest Young's modulus (2.15 GPa) and the lowest modulus belongs to the most flexible member, 6F-PEI-ES (1.07 GPa), in agreement with the observed T$_g$ trend. However, 6FDI-A and PEI-A have even higher moduli, 2.13 and 3.08 GPa, respectively, apparently stemming from effective crosslinking and close packing driven by the inter-chain hydrogen bonding of the COOH pendants.

The morphology of the materials was characterized with wide-angle X-ray diffraction (WAXD). The results indicated that all the polyimides were completely amorphous as evidenced by the featureless diffraction patterns of these materials. Thus, the influence of any crystallinity on the humidity-driven response of these materials is deemed to be negligible.

Solubility:

Eight organic solvents, i.e., ethanol, acetone, CH$_2$Cl$_2$, CHCl$_3$, THF, DMSO, DMAc and NMP, were used to evaluate the solubilities of polyimides and the results are summarized in Table 4 as Example 25. All the polymers are insoluble in ethanol, which was used as a precipitating solvent after chemical imidization. With the exception of BTDI-ES, they are all soluble in polar aprotic solvents such as DMSO, DMAc, and NMP. PEI-ES, 6F-PEI-ES, 6FDI-ES, and PEI-N (Ultem®) are soluble in chlorinated solvents (CH$_2$Cl$_2$, CHCl$_3$). It is noteworthy that the CO$_2$H-containing PI-A's, with higher polarity and hydrogen-bonding capability than other polyimides in this work shows excellent solubility in both THF and acetone, especially the latter which is an uncommon solvent for polyimides.

Film Fabrication:

For ES-containing polyimides, we found that the choice of imidization methods, i.e., chemical and thermal imidization, and conditions had direct impact on the film quality, likely because of the equilibrium nature of poly(amic acid) solution that is sensitive to the imidization conditions and pathways and influences the outcome of polyimide molecular weight. For example, the cast films of PI-ES obtained from chemical imidization in solution at room temperature are creasable while those obtained from thermal imidization at 175° C. are brittle (see Table 2 as Example 23).

Thermally-Derived PI-ES:

Copolyimides by Retro-Michael Reaction: The thermal, solid-state, retro-Michael reaction of ES-PI's with an excellent combination of temperature- and time-dependence (i.e., allowing control of the initiation and extent of reaction), and stereospecificity (i.e., no side reactions) was found to be a simple method to generate a series of copolyimides having the same polymer backbone and containing variable ratio of ES and COOH (A) pendants. Thus, PEI-ES (7a) was selected and its film samples were heated in an oven under N$_2$ at 250° C. at a set of durations (0-16 hrs). The resulting copolyimides are designated as PEI-ES:A-xhr, where xhr corresponds to number of heat-treatment hours at 250° C. In TGA (air) experiments, the samples first started to degrade at 270° C. due to the side-chain cleavage and reached a plateau at 350-440° C. (FIG. 10). Aromatic components degraded above 440° C. The percentage of ester-sulfone to carboxylic acid conversion was calculated based on the weight loss at 400° C., and the results are plotted in FIG. 11. There are two linear degradation processes (0-4 and 4-16 hrs). The conversion rate is much faster between 0 and 4 hrs than 4-16 hrs. About 64% of ester sulfonyl was converted into carboxylic acid in the first 4 hr heating at 250° C. (FIG. 11). Possibly, the rate is lower because of higher concentration of COOH formed to slow down the escape of methylvinylsulfone molecule via the transition state of Michael adduct.

Humidity-Driven Actuation

Water uptake testing was conducted on the all the polymers in an attempt to find the correlation between the water sorption and hygromorphic properties of the films (Table 1 as Example 22). Generally speaking, polar groups such as sulfonyl (—$SO_2$—) and carboxylic acid (—$CO_2H$) groups, increase the polymer's ability to absorb the moisture. BTDI-ES, DSDI-ES, and 6FDI-A show the highest water uptake (about 4.8%). Non-functional polymers (PEI-N and 6FDI-N) absorb the least amount of water in the range of 1.22 and 1.31% while the more polar counterparts in Table 1 have uptake values between 2.39 and 2.86%. Overall, these polyimides have much lower water affinity than perchlorate-doped, electrochemically polymerized polypyrrole (PPy.$ClO_4$; 9.9% uptake at 94% RH) and Nafion (15-25% uptake).

Figure 12:
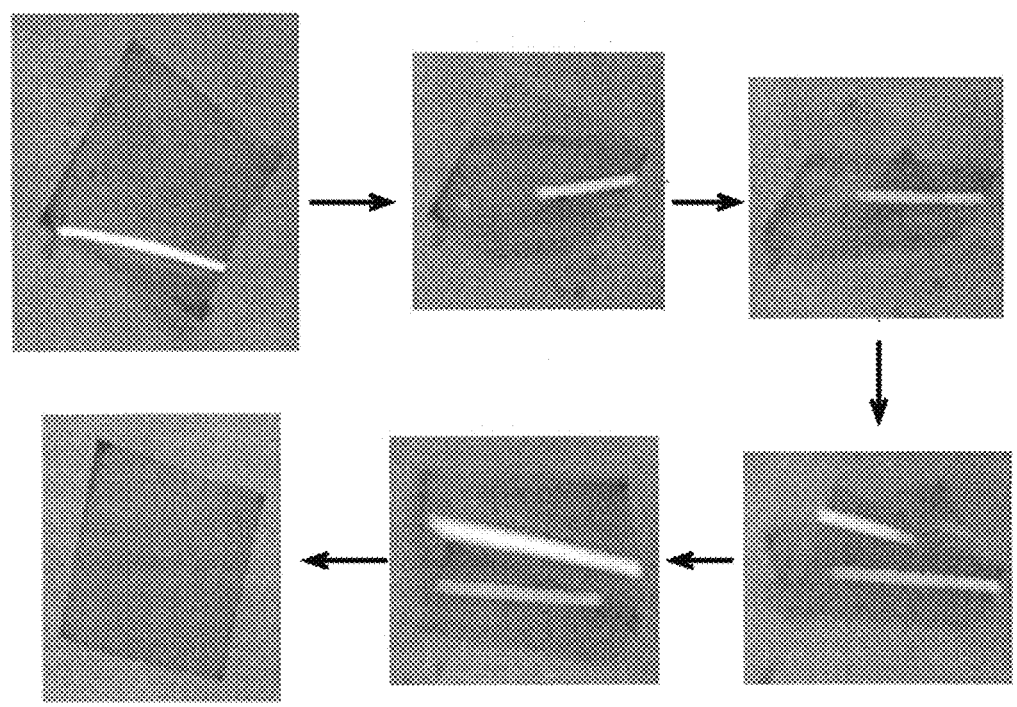
FIG. 12 shows a series of photographs to illustrate a water-gradient actuation and locomotion of a PEI-ES PI film (3 cm×3 cm×30 um) on a piece of wet paper towel, in accordance with an embodiment of the present invention.

Previous comparisons by others of the mechanochemical behavior of PPy.$ClO_4$ films made of non-ionic polymers such as polyolefin, polyester, nylon, and polystyrene and reported that no noticeable humidity induced deformation. However, it has been observed that a thin polymer film (about 3 cm×3 cm and 30 m thick) of PEI-ES (also non-ionic) has the ability to be self-actuating and locomotive on a wet surface (See FIG. 12, where arrows designate sequential photographs). Briefly, upon being laid flat on a piece of water-wet paper towel, two opposite parts of the film were able to curl up like a pair of wings while standing still, and then moved to another spot by flipping over when the "wings" are in close contact, following by a quick roll-over and flattening action. The apparently self-propelling movement continued across the wet surface until when the film reached the edge of the humidity field. In addition, we found that similarly fabricated film from an unmodified poly(ether-imide) (Ultem®) or a highly hygroscopic polymer, namely Nafion, were practically unresponsive under the same testing conditions. Apparently, the former lacks suitable functional group with high affinity for polar molecules (e.g., $H_2O$ and MeOH), and the water molecules are known to tenaciously bind to the sulfonic acid groups in the latter at room temperature.

Figure 13:
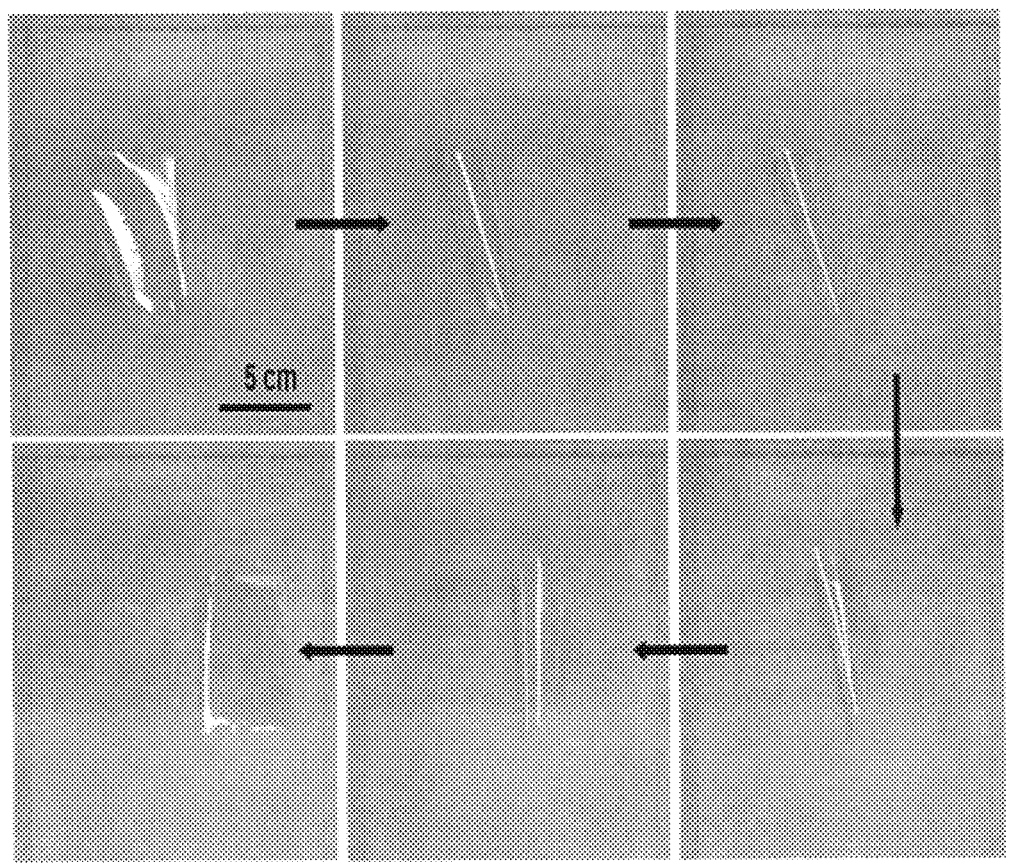
FIG. 13 shows a series of photographs to illustrate the water-gradient actuation and locomotion of a 6FDI-A PI film on a piece of wet paper towel, in accordance with an embodiment of the present invention.

During the course of this work, it became apparent that amorphous polymers containing other simple and highly polar moieties such as COOH pendants can be hygromorphic and motile as well under non-equilibrating humidity conditions. A series of representative snapshots of the actuation and locomotion sequence of the 6FDI-A film is depicted in FIG. 13.

Figures 14A, 14B:
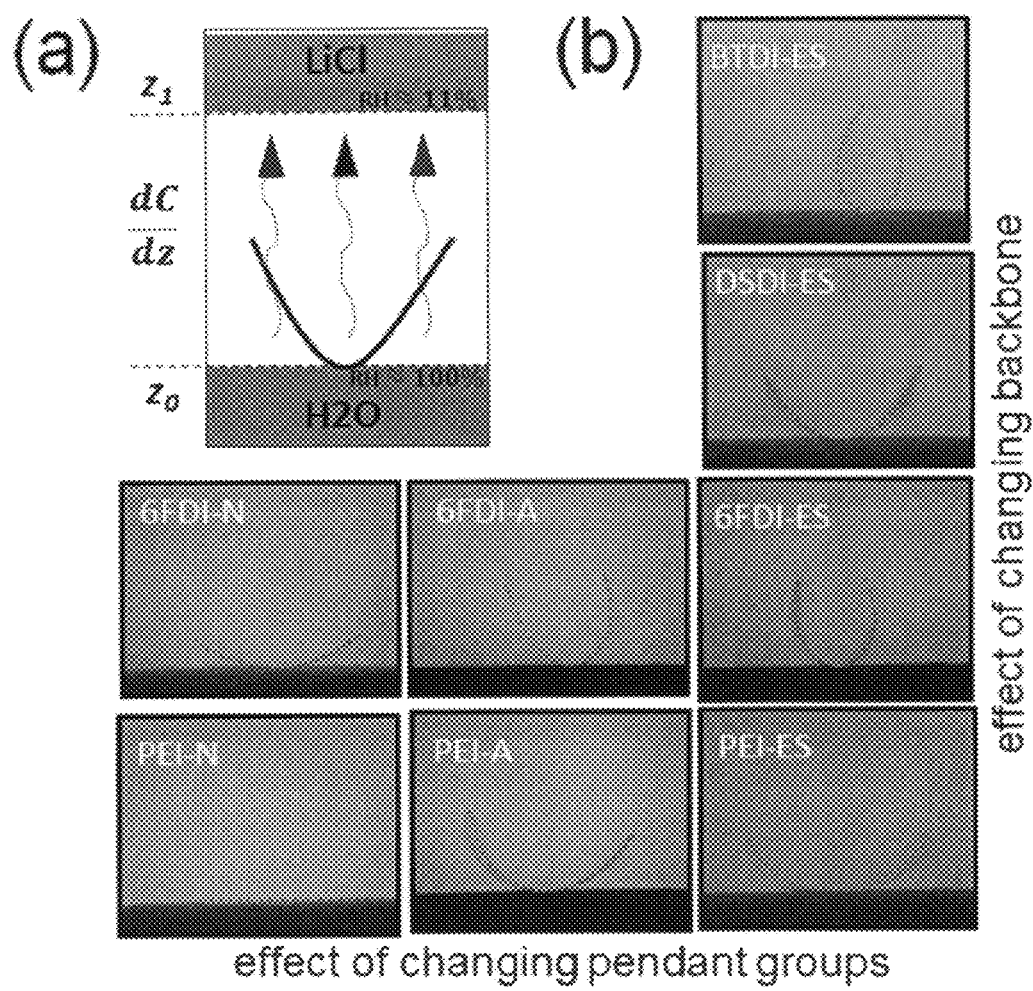
FIGS. 14a and 14b demonstrate how a humidity gradient drives film curvature, where

Humidity Gradient Actuation Assessment:

A steady state humidity response of circular films with diameter of 2.7 cm was quantified using a custom built humidity gradient chamber. The humidity gradient was generated by using deionized water as the source and a saturated aqueous solution of lithium chloride (LiCl (aq)) as the sink. The separation between the source and the sink was maintained at 4 cm. Deionized water generates an equilibrium relative humidity of 100% while LiCl (aq) generates an equilibrium relative humidity of 11% (see FIG. 14A). Therefore, a linear estimate of the steady state humidity gradient is about 22%/cm. The films were placed in the chamber and the equilibrium curvature of the discs was imaged.

No actuation was observed in the absence of a humidity gradient, as tested by using deionized water as the source and sink. However, under a constant flux of water vapor from the source, the films actuated and maintained a constant conformation. The relative actuation was observed to be dependent on the molecular configuration. Overall, the presence of hydrophilic groups in the polymer structure had a positive effect on actuation when compared to films containing no hydrophilic polymer backbone or side chain, e.g., PEI-ES vs PEI-N (see FIG. 14B). While both PEI-N and 6FDI-N contains no hydrophilic pendants, the 6FDI-N backbone has been reported to be rather hydrophilic, and would account for the observed curvature angle (vs. zero curvature for PEI-N), which is still smaller than those polyimides containing hydrophilic pendants and being hygromorphic/motile. When the rigidity of the backbone increased, with the pendant groups remaining unchanged, a general increase in the actuation was observed FIG. 14B. 6FDI-ES somewhat falls out of line likely because of the added effect of its relatively more hydrophilic backbone as noted for 6FDI-N. There were slight changes in the film curvature when the pendant group was changed from ester-sulfone to carboxylic acid. The effect of pendant groups and backbone architecture on film curvature can be visualized in FIG. 14B. Together, these results highlight that humidity-driven actuation can be generated from a non-ionic polymer by simply grafting a sufficient amount of highly polar methylsulfonylethyl ester groups to the PEI backbone. Advantages of our approach include the convenient solubility of PEI polymer and the monolithic nature of the product, which eliminates phase separation or other interfacial issues of a multi-component system.

While the present invention has been illustrated by the description of one or more embodiments thereof, and while the embodiments have been described in considerable detail, they are not intended to restrict or in any way limit the scope of the appended claim to such detail. Additional advantages and modification will be readily apparent to those skilled in the art. The invention in its broader aspects is therefore not limited to the specific details, representative apparatus and methods and illustrative examples shown and described. Accordingly, departures may be made from such details without departing from the scope or the spirit of the general inventive concept exemplified herein.

What is claimed is:

1. A polymer comprising:
a diamine portion derived from an aryl diamine monomer comprising a sulfone moiety and having a general chemical formula:

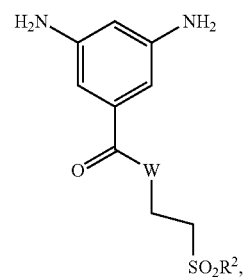

wherein W is selected from the group consisting of O, NH, and $NR^1$;

wherein R¹ and R² are independently selected from the group consisting of substituted or unsubstituted C1-C7 alkyl groups and unsubstituted phenyl groups;

and wherein the polymer is selected from the group consisting of a polyamide, a polyimide, and a poly(amide-imide).

2. The polymer of claim 1, wherein the polyimide is selected from the group consisting of an ester-sulfone-containing polyimide and an amide-sulfone-containing polyimide, the polymer having a general chemical formula:

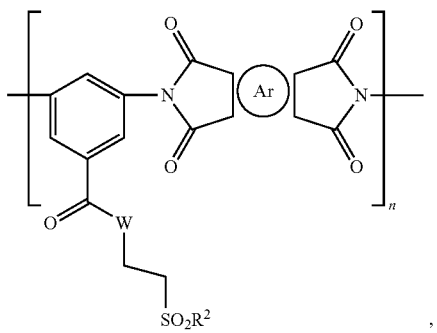

wherein when W is O, then the moiety is an ester-sulfone, and when W is NH or NR, then the moiety is an amide-sulfone, wherein

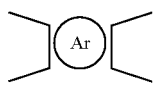

is selected from the group consisting of

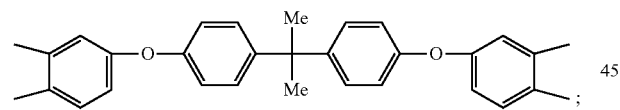

a. BPADA

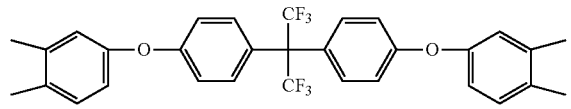

b. 6F-BPADA

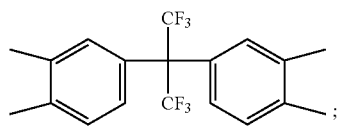

c. 6FDA

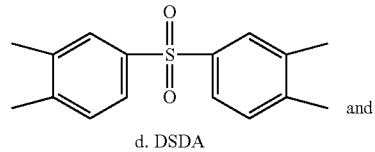

d. DSDA and

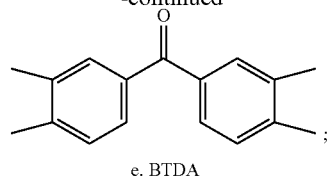

e. BTDA and wherein n represents a degree of polymerization.

3. The polymer of claim 1, wherein the polyamide is selected from the group consisting of an ester-sulfone-containing polyamide and an amide-sulfone-containing polyamide, the polymer having a general chemical formula:

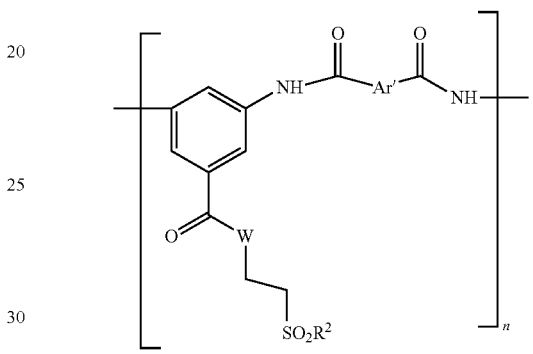

wherein Ar' is selected from the group consisting of

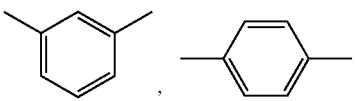

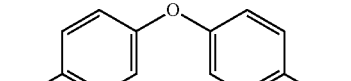

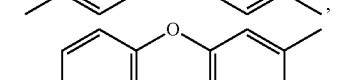

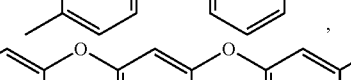

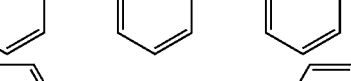

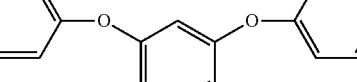

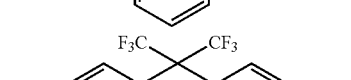

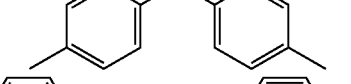

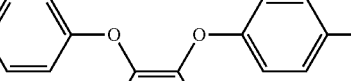

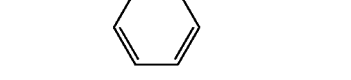

and

-continued

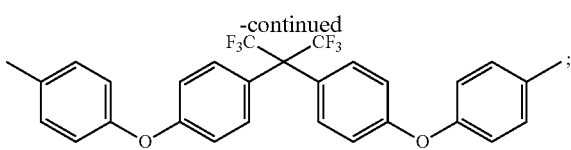

and wherein n represents a degree of polymerization.

4. The polymer of claim 1, wherein the poly(amide-imide) is selected from the group consisting of an ester-sulfone-containing poly(amide-imide) and an amide-sulfone-containing poly(amide-imide), the polymer having a general formula:

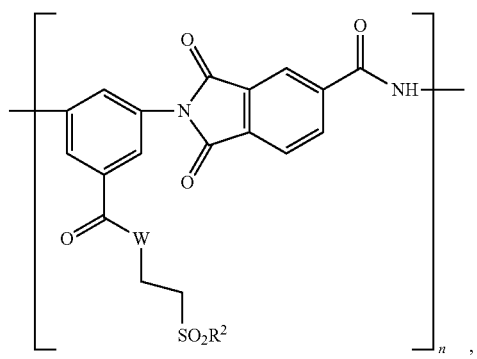

wherein n represents a degree of polymerization.

5. The polymer of claim 1, wherein the poly(amide-imide) is selected from the group consisting of an ester-sulfone-containing poly(amide-imide) and an amide-sulfone-containing poly(amide-imide), the polymer having a general chemical formula:

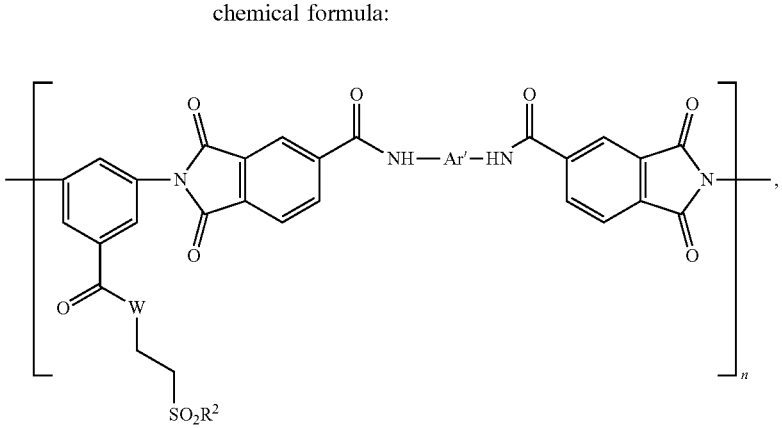

wherein Ar' is selected from the group consisting of

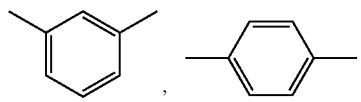

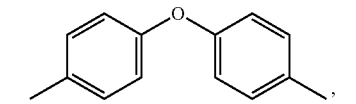

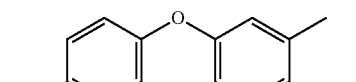

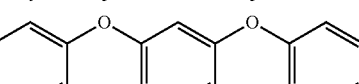

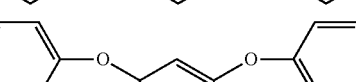

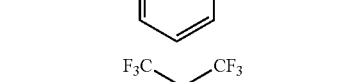

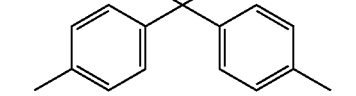

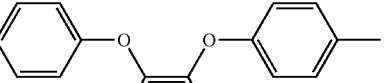

and

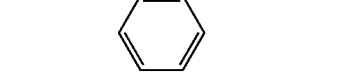

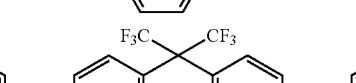

and wherein n represents a degree of polymerization.

6. The polymer of claim 1, wherein the poly(amide-imide) is selected from the group consisting of an ester-sulfone-containing poly(amide-imide) and an amide-sulfone-containing poly(amide-imide), the polymer having a general chemical formula:

wherein Ar' is selected from the group consisting of

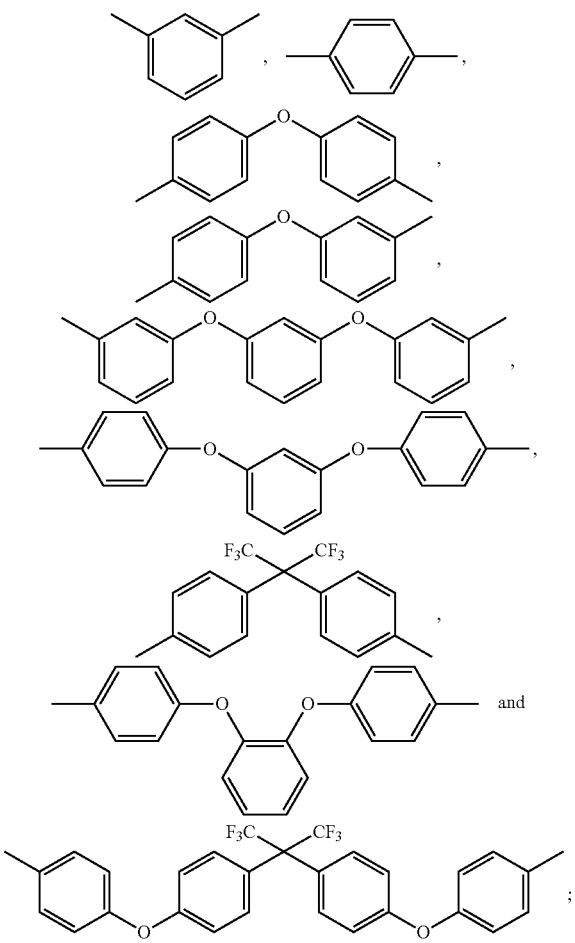

and wherein n represents a degree of polymerization.

7. A copolymer composition comprising complementary monomer portions of a first monomer portion comprising a sulfone terminated pendant group and having a general chemical formula:

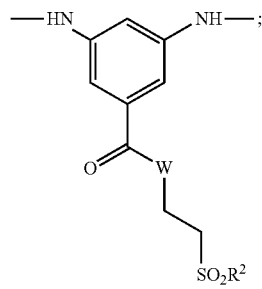

and a second monomer portion comprising at least one carboxylic acid or carboxamide terminated pendant group and having a general chemical formula:

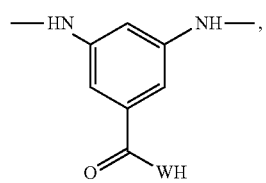

wherein W is selected from the group consisting of O, NH, and $NR^1$;

wherein $R^1$ and $R^2$ are independently selected from the group consisting of substituted or unsubstituted C1-C7 alkyl groups, and substituted or unsubstituted phenyl groups;

and wherein the copolymer is selected from the group consisting of a polyamide copolymer, a polyimide copolymer, and a poly(amide-imide) copolymer.

8. The copolymer composition of claim 7, wherein the copolymer is a polyimide copolymer comprising complementary portions of the sulfone terminated pendant group and the at least one carboxylic acid or carboxamide terminated pendant group, the polyimide copolymer having a general chemical formula:

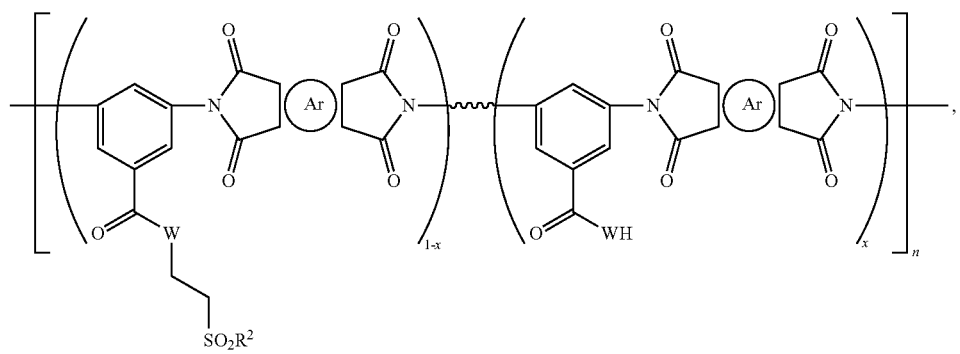

wherein

is selected from the group consisting of

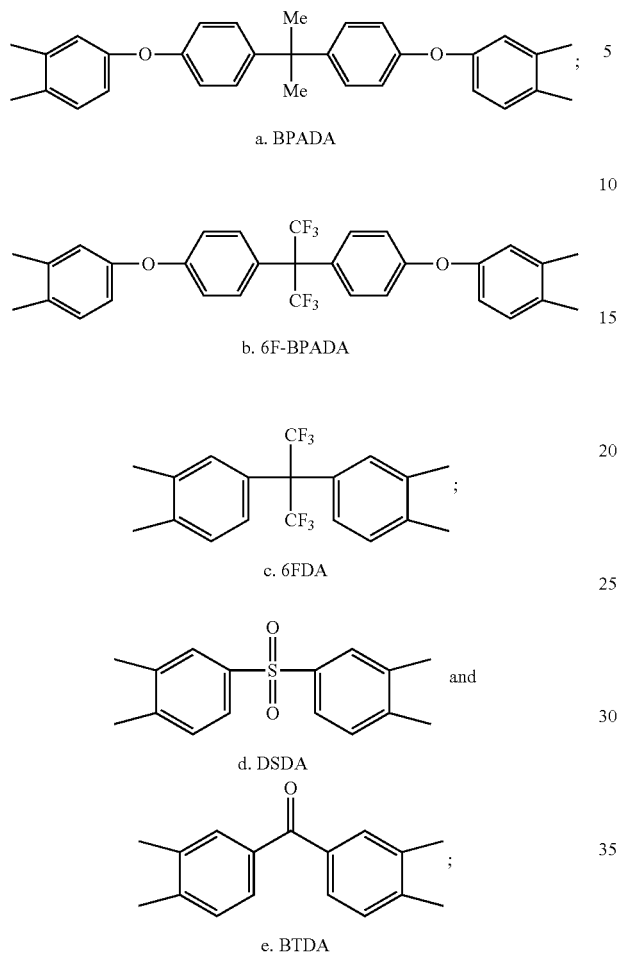

a. BPADA b. 6F-BPADA c. 6FDA d. DSDA and e. BTDA and n represents a degree of polymerization; and wherein x is in a range of about 0.01 to about 0.99.

9. The copolymer composition of claim 7, wherein the copolymer is a polyamide copolymer comprising complementary portions of a sulfone terminated pendant group and at least one carboxylic acid or carboxamide terminated pendant group, the polyamide copolymer having a general chemical formula:

wherein Ar' is selected from the group consisting of

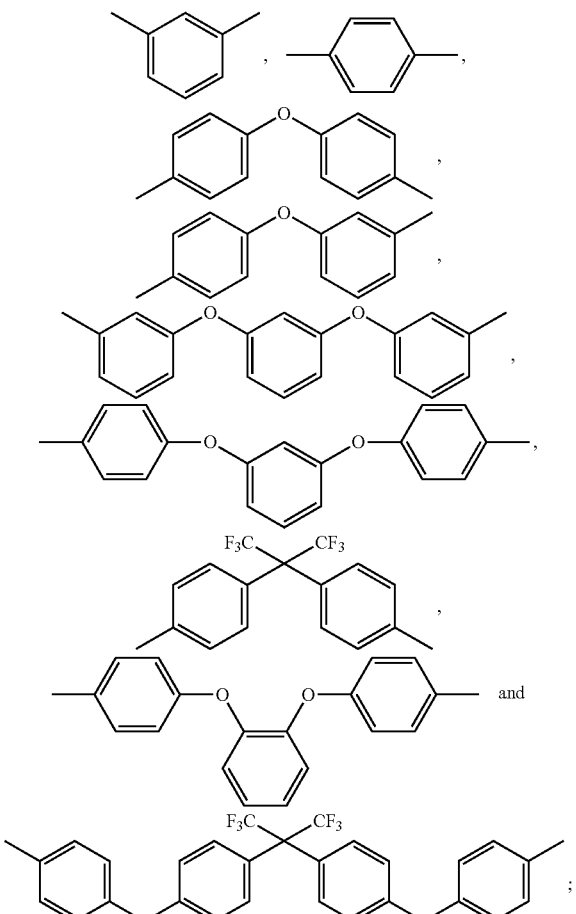

and wherein n represents a degree of polymerization, and wherein x is in a range of about 0.01 to about 0.99.

10. The copolymer composition of claim 7, wherein the copolymer is a poly(amide-imide) copolymer comprising complementary portions of a sulfone terminated pendant group and at least one carboxylic acid or carboxamide terminated pendant group, the poly(amide-imide) copolymer having a general chemical formula:

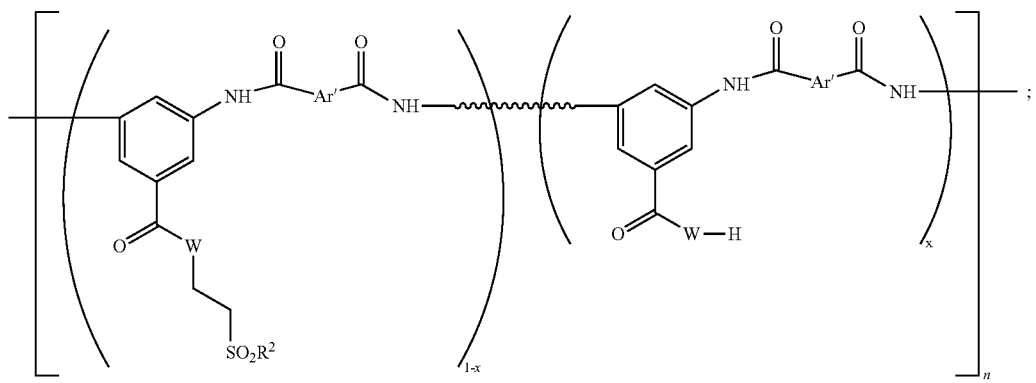

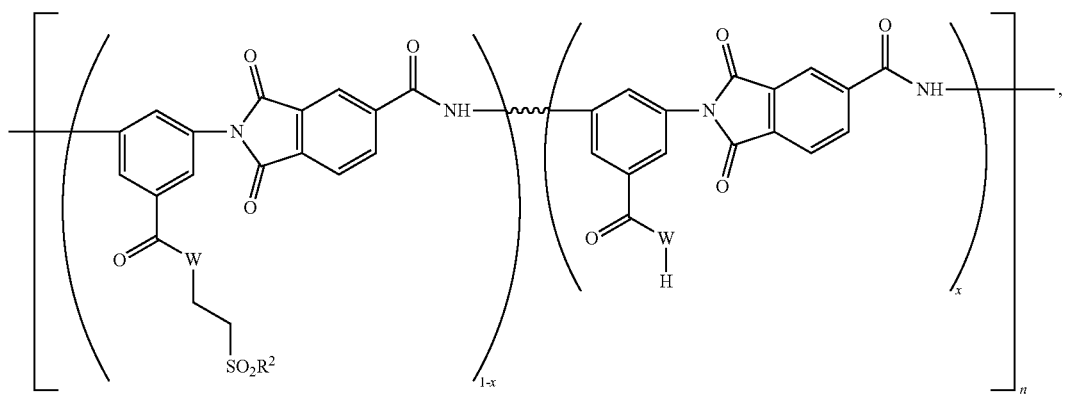

wherein n represents a degree of polymerization; and
wherein x is in a range of about 0.01 to about 0.99.

11. The copolymer composition of claim 7, wherein the copolymer is a poly(amide-imide) copolymer comprising complementary portions of a sulfone terminated pendant group and at least one carboxylic acid or carboxamide terminated pendant group, the copolymer having a general chemical formula:

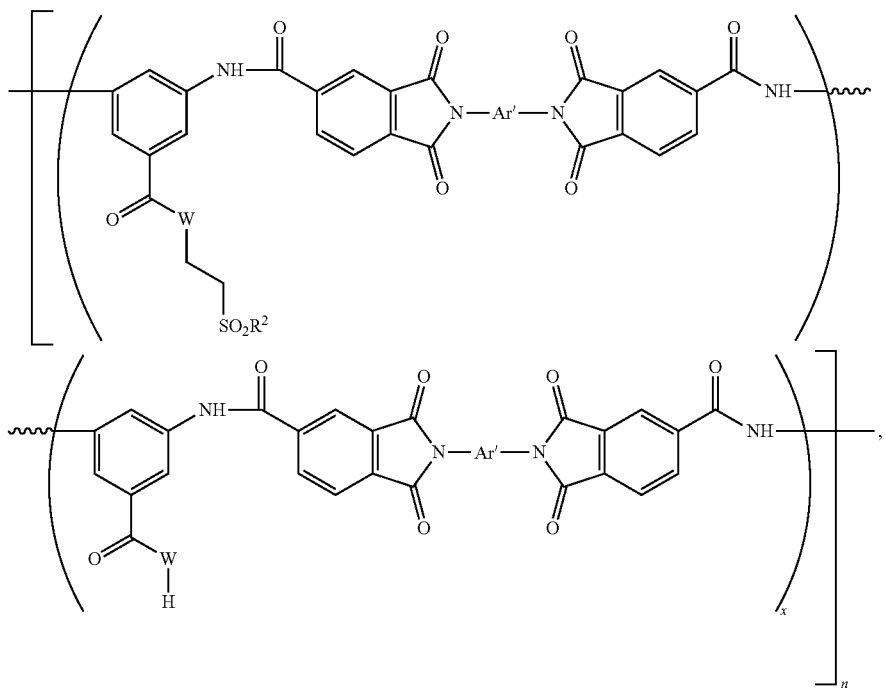

wherein Ar' is selected from the group consisting of

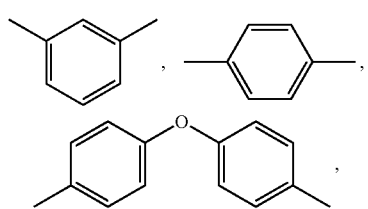

-continued

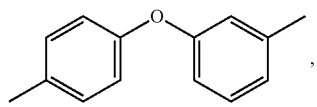

-continued

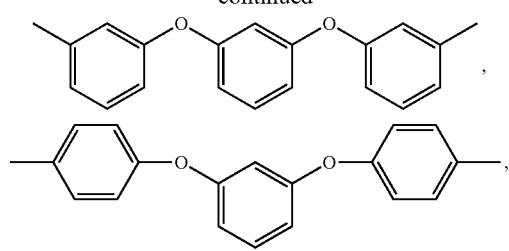

-continued

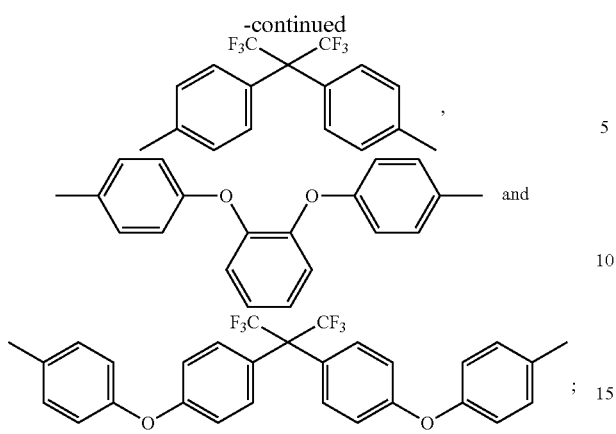

and wherein n represents a degree of polymerization; and wherein x is in a range of about 0.01 to about 0.99.

12. The copolymer composition of claim 7, wherein the copolymer is a poly(amide-imide) copolymer composition comprising complementary portions of a sulfone terminated pendant group and at least one carboxylic acid or carboxamide terminated pendant group, the copolymer having a general chemical formula:

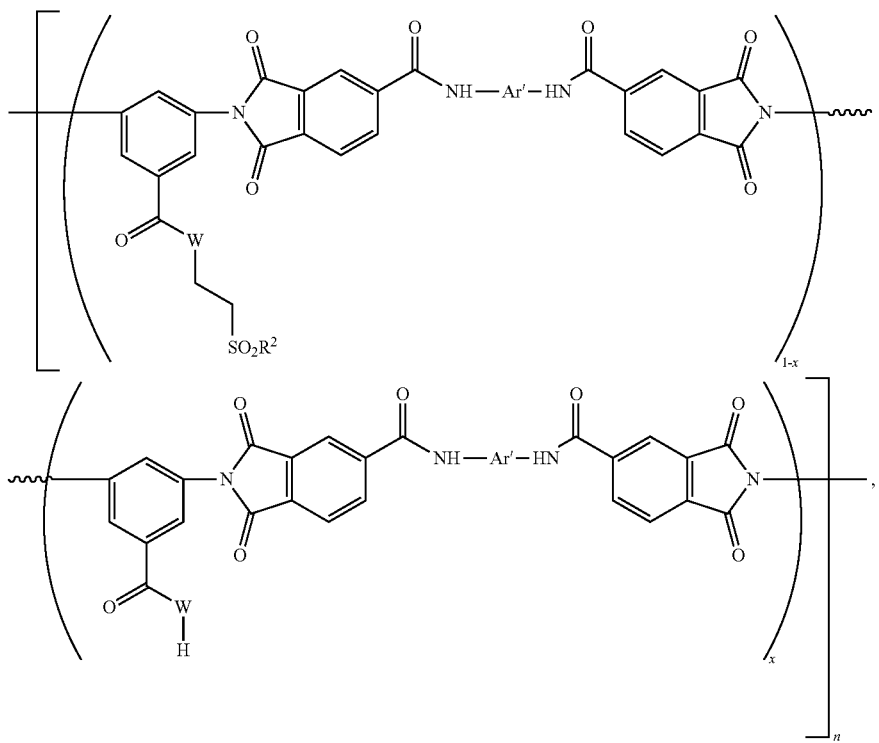

wherein Ar' is selected from the group consisting of

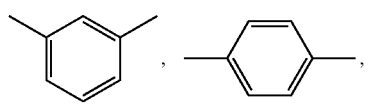

-continued

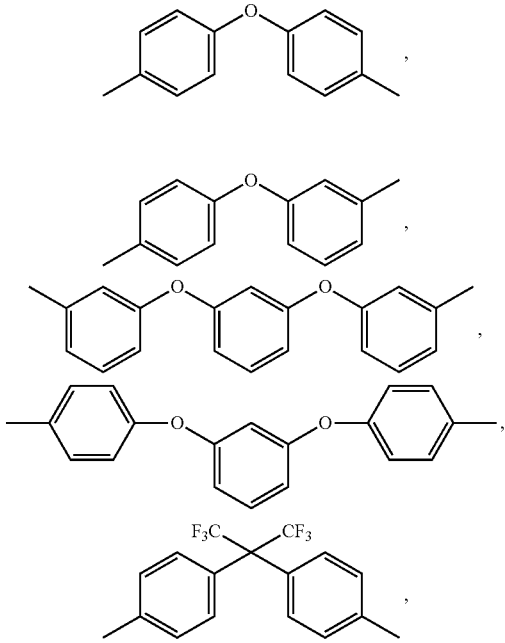

-continued

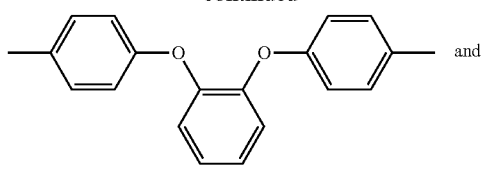

and

-continued

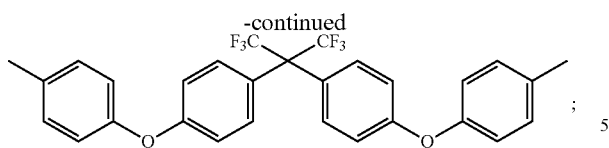

and
wherein n represents a degree of polymerization; and
wherein x is in a range of about 0.01 to about 0.99.

13. A method of making the copolymer composition of claim 7, comprising:
heating a polymer comprising the first monomer portion comprising the sulfone terminated pendant group above a thermal degradation temperature to induce a retro-Michael reaction to provide the second monomer portion comprising at least one carboxylic acid or carboxamide terminated pendant group by an elimination of a vinyl sulfone moiety that has a general formula:

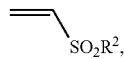

wherein the polymer is selected from the group consisting of a polyamide, a polyimide, and a poly(amide-imide).

* * * * *